(12) United States Patent
Werner-Simon et al.

(10) Patent No.: US 10,723,766 B2
(45) Date of Patent: Jul. 28, 2020

(54) DERIVATIVES OF GAMMA-AMANITIN

(71) Applicant: Heidelberg Pharma Research GmbH, Ladenburg (DE)

(72) Inventors: Susanne Werner-Simon, Hüffelsheim (DE); Christian Lutz, Weinheim (DE); Christoph Müller, München (DE); Werner Simon, Hüffelsheim (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 63 days.

(21) Appl. No.: 15/779,510

(22) PCT Filed: Nov. 28, 2016

(86) PCT No.: PCT/EP2016/078984
§ 371 (c)(1),
(2) Date: May 25, 2018

(87) PCT Pub. No.: WO2017/089607
PCT Pub. Date: Jun. 1, 2017

(65) Prior Publication Data
US 2018/0346519 A1    Dec. 6, 2018

(30) Foreign Application Priority Data

Nov. 27, 2015    (EP) ..................... 15003389

(51) Int. Cl.
C07C 1/06        (2006.01)
C07K 7/64        (2006.01)
(Continued)

(52) U.S. Cl.
CPC .............. C07K 7/64 (2013.01); C07C 227/16 (2013.01); C07C 229/22 (2013.01);
(Continued)

(58) Field of Classification Search
CPC ... C07K 7/64; C07K 1/10; C07K 1/06; C07K 1/065; C07C 229/22; C07C 227/16; C07C 271/22; C07C 2603/18
See application file for complete search history.

(56) References Cited

FOREIGN PATENT DOCUMENTS

| CN | 102459160 A | 5/2012 |
|---|---|---|
| EP | 2 497 499 A1 | 9/2012 |

(Continued)

OTHER PUBLICATIONS

International Search Report, International Application No. PCT/EP2016/078984 (published as WO 2017/089607), 3 pages (dated Feb. 13, 2017).

(Continued)

*Primary Examiner* — Sudhakar Katakam
(74) *Attorney, Agent, or Firm* — Prismatic Law Group, PLLC

(57) ABSTRACT

The invention relates to γ-amaninamide (1; x=0, 1 or 2), γ-amaninamidic acid (2; x=0, 1 or 2), and γ-amaninamidic hydroxamic acid (3; x=0, 1 or 2), novel derivatives of γ-amanitin (4), and methods and novel building blocks for the synthesis thereof.

(Continued)

-continued

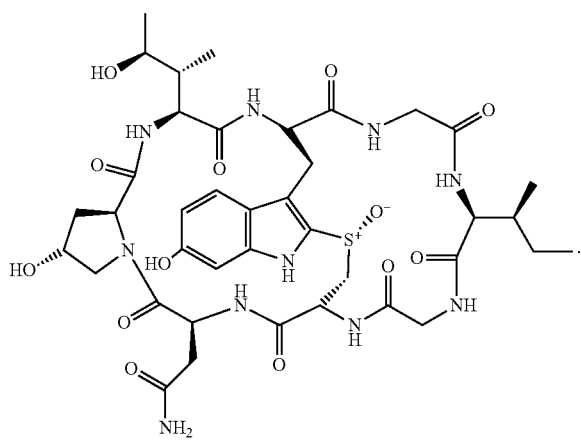

4 Claims, 11 Drawing Sheets

(51) Int. Cl.
C07C 271/22 (2006.01)
C07K 1/06 (2006.01)
C07C 229/22 (2006.01)
C07K 1/10 (2006.01)
C07C 227/16 (2006.01)

(52) U.S. Cl.
CPC .............. C07C 271/22 (2013.01); C07K 1/06 (2013.01); C07K 1/065 (2013.01); C07K 1/10 (2013.01); *C07C 2603/18* (2017.05)

(56) References Cited

FOREIGN PATENT DOCUMENTS

EP 2 684 865 A1 1/2014
WO WO-2014009025 A1 * 1/2014 ........... C07C 229/22

OTHER PUBLICATIONS

Shoham et al., "Crystal and Molecular Structure of S-Deoxo[Ile3]amaninamide: A Synthetic Analogue of Amanita Toxins," J. Am. Chem Soc., vol. 106, No. 16, pp. 4606-4615 (Aug. 1984).

Zanotti et al., "Structure-toxicity relationships in the amatoxin series. Synthesis of S-deoxy[γ(R)-hydroxy-Ile3]-amaninamide, its crystal and molecular structure and inhibitory efficiency," Int. J. Peptide Protein Res., vol. 34, pp. 222-228 (1989).

Zhao et al., "Synthesis of a Cytotoxic Amanitin for Biorthogonal Conjugation," Chembiochem, vol. 16, No. 10, pp. 1420-1425 (Jun. 3, 2015).

* cited by examiner

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |
| γ-amanin | H | OH | OH | H |
| γ-amaninamide | H | OH | NH2 | H |

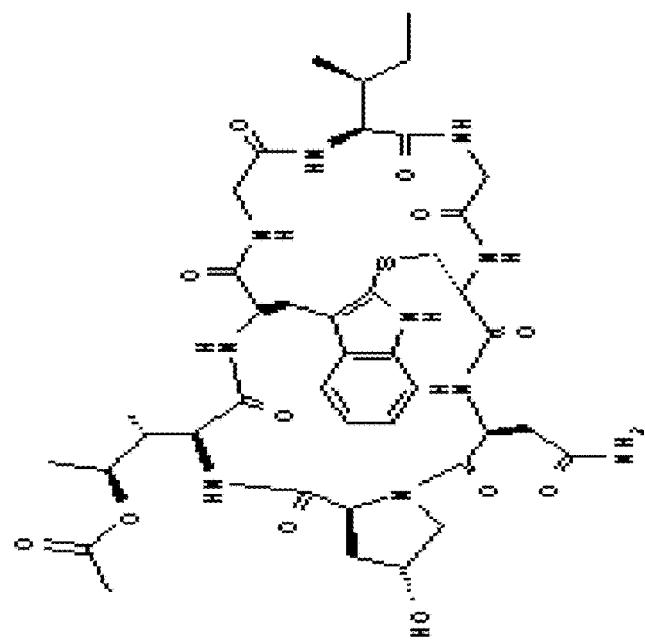
Figure 2 (f)
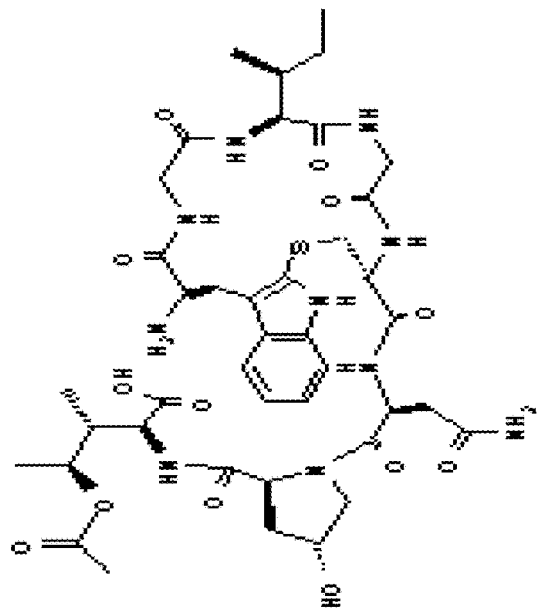

▲: γ-Amanitin

■: synthetic γ-Amaninamid HDP 30.1790

DERIVATIVES OF GAMMA-AMANITIN

CROSS-REFERENCE TO RELATED APPLICATIONS

This application is a 371 national phase of International Application No. PCT/EP2016/078984 filed Nov. 28, 2016, which claims priority to European Application No. 15003389.2 filed Nov. 27, 2015, each of which applications is herein incorporated by reference in its entirety.

FIELD OF THE INVENTION

The invention relates to γ-amaninamide (1; x=0, 1 or 2), γ-amaninamidic acid (2; x=0, 1 or 2), and γ-amaninamidic hydroxamic acid (3; x=0, 1 or 2), novel derivatives of γ-amanitin (4), and methods and novel building blocks for the synthesis thereof.

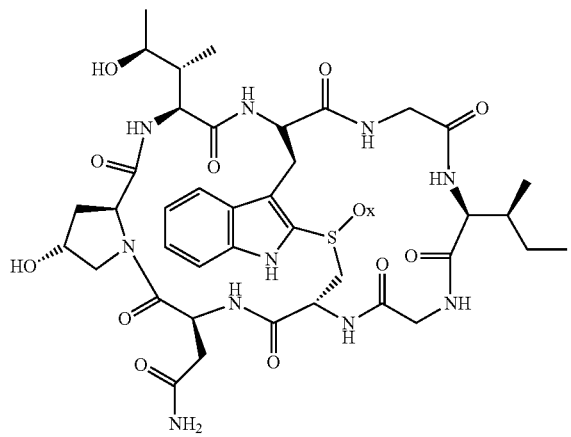

1

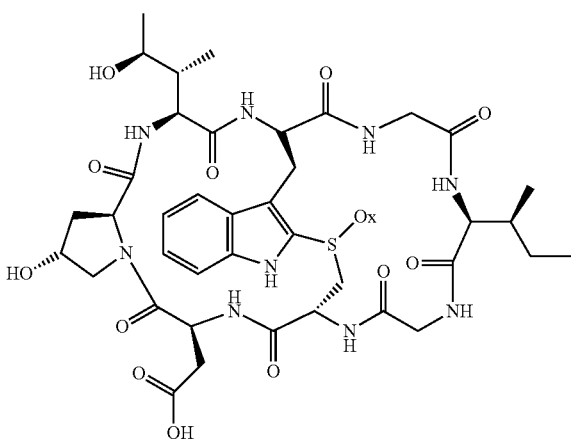

2

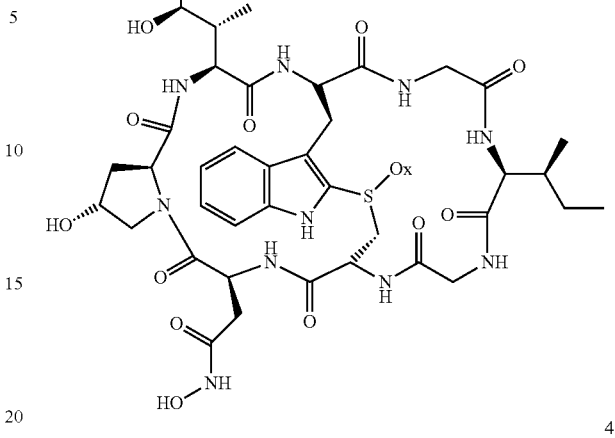

3

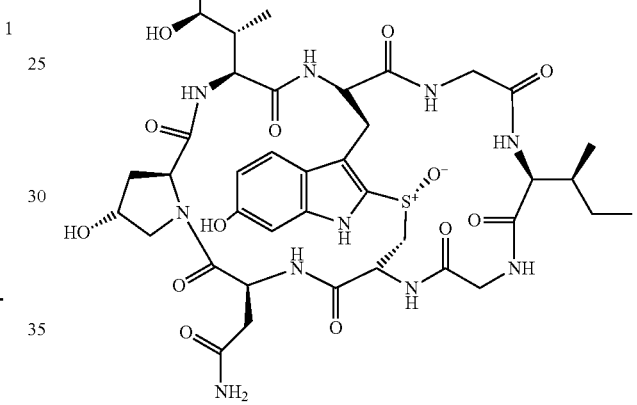

4

BACKGROUND OF THE INVENTION

Amatoxins are cyclic peptides composed of 8 amino acids that are found in *Amanita phalloides* mushrooms (see FIG. 1). Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumour therapy had already been explored in 1981 by coupling an anti-Thy 1.2 antibody to α-amanitin using a linker attached to the indole ring of Trp (amino acid 4; see FIG. 1) via diazotation (Davis & Preston, Science 213 (1981) 1385-1388). Davis & Preston identified the site of attachment as position 7'. Morris & Venton demonstrated as well that substitution at position 7' results in a derivative, which maintains cytotoxic activity (Morris & Venton, Int. J. Peptide Protein Res. 21 (1983) 419-430).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji) and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the amatoxins, were provided.

Patent applications WO 2010/115629 and WO 2010/115630 (both published Oct. 14, 2010) describe conjugates, where antibodies, such as anti-EpCAM antibodies such as humanized antibody huHEA125, are coupled to amatoxins via (i) the γ C-atom of amatoxin amino acid 1, (ii) the 6' C-atom of amatoxin amino acid 4, or (iii) via the δ C-atom of amatoxin amino acid 3, in each case either directly or via a linker between the antibody and the amatoxins. The suggested linkers comprise elements such as amide, ester, ether, thioether, disulfide, urea, thiourea, hydrocarbon moieties and the like. Furthermore, the inhibitory effects of these conjugates on the proliferation of breast cancer cells (cell line MCF-7), pancreatic carcinoma (cell line Capan-1), colon cancer (cell line Colo205), and cholangiocarcinoma (cell line OZ) were shown.

Amatoxins can be isolated from collected *Amanita phalloides* mushrooms fruit bodies, or from pure cultures (Zhang P, Chen Z, Hu J, Wei B, Zhang Z, and Hu W, Production and characterization of Amanitin toxins from a pure culture of *Amanita exitialis*, FEMS Microbiol Lett. 2005 Nov. 15; 252(2):223-8. Epub 2005 Sep. 15). However, the amounts of amatoxins that can be obtained are rather low (in the range of about 0.3-3 mg/g dry matter from natural fruit bodies, and about 10% thereof from pure culture) and the flexibility for further modifying the naturally occurring amatoxin variants is limited (see references discussed in [003]-[005] and references cited therein).

Alternatively, amatoxins can be obtained from fermentation using a basidiomycete (Muraoka S, and Shinozawa T., Effective production of amanitins by two-step cultivation of the basidiomycete, *Galerina fasciculata* GF-060, J Biosci Bioeng. 2000; 89(1):73-6; the reported yield was about 5 mg/l culture) or *A. fissa* (Guo X W, Wang G L, and Gong J H, Culture conditions and analysis of amanitins on *Amanita spissa*, Wei Sheng Wu Xue Bao. 2006 June; 46(3):373-8; the reported yield was about 30 μg/l culture). Again, yields are low, and flexibility for further modifying the naturally occurring amatoxin variants is limited as well.

Finally, amatoxins have been prepared by partial or total synthesis (e.g. Zanotti G, Möhringer C, and Wieland T., Synthesis of analogues of amaninamide, an amatoxin from the white *Amanita virosa* mushroom, Int J Pept Protein Res. 1987 October; 30(4):450-9; Zanotti G, Wieland T, Benedetti E, Di Blasio B, Pavone V, and Pedone C., Structure-toxicity relationships in the amatoxin series. Synthesis of 5-deoxy [gamma(R)-hydroxy-Ile3]-amaninamide, its crystal and molecular structure and inhibitory efficiency, Int J Pept Protein Res. 1989 September; 34(3):222-8; Zanotti G, Petersen G, and Wieland T., Structure-toxicity relationships in the amatoxin series. Structural variations of side chain 3 and inhibition of RNA polymerase II, Int J Pept Protein Res. 1992 December; 40(6):551-8; Zhao et al., Synthesis of a Cytotoxic Amanitin for Biorthogonal Conjugation, ChemBioChem 16 (2015) 1420-1425).

It is worth noting that Zanotti et al., 1989 (loc. cit.) reports the synthesis of the biologically inactive S-deoxo-γ(R)-hydroxy-isoleucin-amaninamide, while the synthesis of the active enantiomer has apparently not been successful.

Furthermore, Zhao et al. (loc. cit) report the synthesis of a γ-amaninamide derivative starting from 4(S)-4-hydroxyisoleucin. The authors, however, identified that the resulting γ-amaninamide derivative was only of negligible toxicity and thus taught away from further developing such γ-amaninamide-based structures.

While the use of fully-synthetic routes to amatoxins may offer an option for the supply of larger quantities of amatoxins required for therapeutic uses, and may offer the construction of a variety of novel α- or β-amatoxin variants by using appropriate starting materials as building blocks, the approaches pursued in the past had been limited by the fact that an essential building block, γ,δ-dihydroxyisoleucine, or a synthon therefor, had not been available as pure diastereomer. While WO 2014/009025 describes a novel synthon for γ,δ-dihydroxyisoleucine and its use for the synthesis of amatoxins, such approach is nevertheless expensive and labor-extensive.

OBJECT OF THE INVENTION

Thus, there was still a great need for a cost-efficient and robust way of synthesizing amatoxins. In particular, there is a strong need for alternatives to the amatoxin conjugates based on α and β-amanitins, for which no fully satisfactory synthetic access has been identified so far.

SUMMARY OF THE INVENTION

The present invention is based on the unexpected observation that readily available (2S,3R,4S)-L-4-hydroxyisoleucine (5)

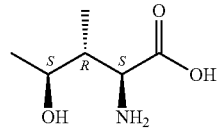

can be protected by an orthogonal protection strategy and can be used for the synthesis of amatoxins having γ-hydroxyisoleucine as amino acid 3.

Thus, in one aspect the present invention relates to a compound, which is a derivative of (2S,3R,4S)-L-4-hydroxyisoleucine (structure 5), having the structure (2S,3R,4S)—CH$_3$—CH(OR$^1$)—CH(CH$_3$)—CH(NHR$^2$)—C(=O) OR$^3$ (structure 6), wherein R$^1$ and R$^3$ are stable under conditions, where R$^2$ can be cleaved off, and R$^1$ and R$^2$ are stable under conditions, where R$^3$ can be cleaved off, in particular wherein R$^1$ is alkanoyl, particularly acetyl or CH$_3$COCH$_2$CO—, R$^2$ is Fmoc and R$^3$ is benzyl or t-butyl.

In a second aspect, the present invention relates to a method for synthesizing a compound of structure 6 (2S,3R,4S)—CH$_3$—CH(OR$^1$)—CH(CH$_3$)—CH(NHR$^2$)—C(=O) OR$^3$, comprising the steps of (a) complexing the compound of structure 5 with copper or boron, in particular with 9-borabicyclo [3,3,1] nonan (9-BBN); (b) acylation of the 4-hydroxy group with a compound R$^{1'}$—C(=O)—X, wherein X is a leaving group, particularly wherein R$^{1'}$ is alkyl, particularly C$_{1-6}$-alkyl, particularly methyl; (c) cleavage of the metal complex; (d) protection of the α-amino group with an R$^2$ group, particularly an Fmoc group; and (e) protection of the carboxyl group with an R$^3$ group, particularly a benzyl or t-butyl group.

Scheme 1 (6*: structure 6 with $R^1$ = Me; $R^2$ = Fmoc; $R^3$ = benzyl):

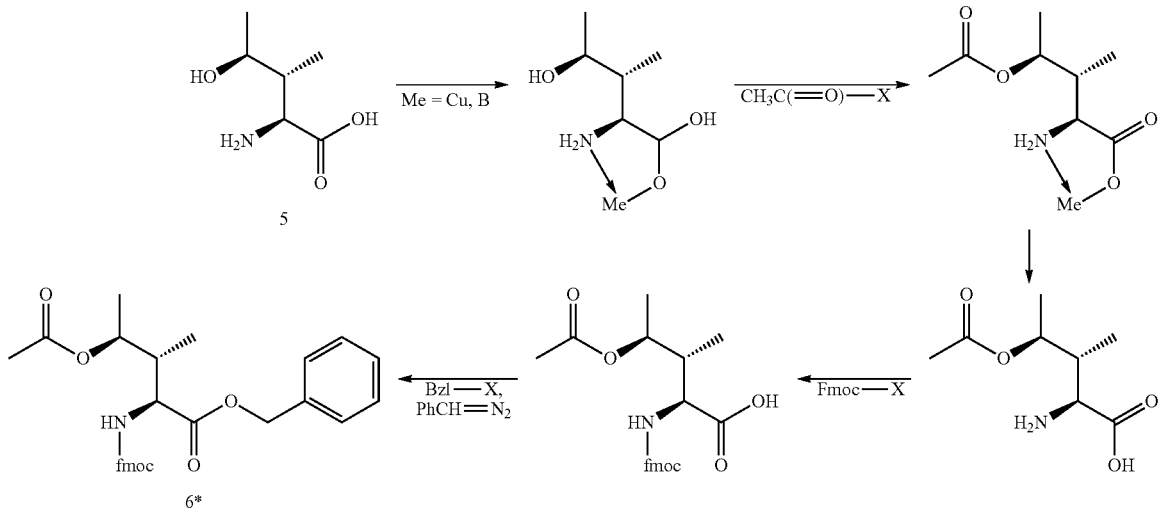

In a third aspect, the present invention relates to a kit comprising a compound of structure 6, and at least one additional reagent for the synthesis of amatoxins or precursors thereof.

In a fourth aspect, the present invention relates to a method for synthesizing an amatoxin, or precursor molecule therefor, comprising the steps of (a1) cleaving protection group $R^2$ from a compound of structure 6 (2S,3R,4S)—$CH_3$—$CH(OR^1)$—$CH(CH_3)$—$CH(NHR^2)$—$C(=O)OR^3$, and (a2) coupling of the deprotected variant of 6 with a free amino group obtained according to step (a1) to an activated variant of hydroxyproline, a protected variant thereof or synthon therefor, particularly to a compound of a structure selected from 7, 8 and L.

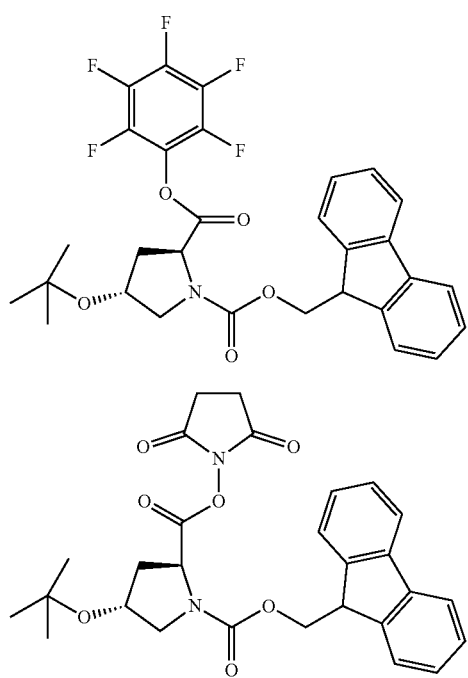

7

-continued

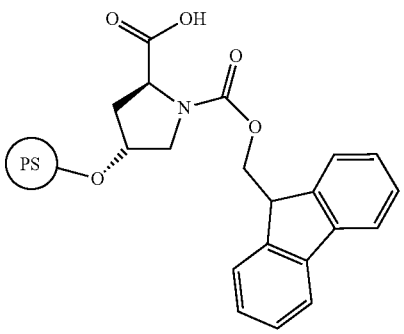

L

In a fifth aspect, the present invention relates to γ-amaninamide (1; x=0, 1 or 2), γ-amaninamidic acid (2; x=0, 1 or 2), and γ-amaninamidic hydroxamic acid (3; x=0, 1 or 2).

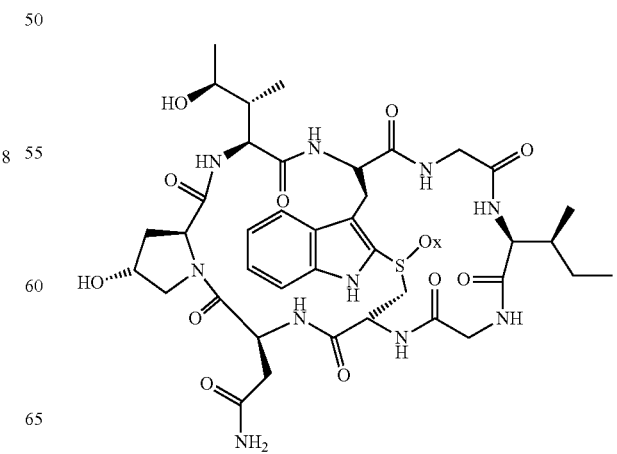

8

1

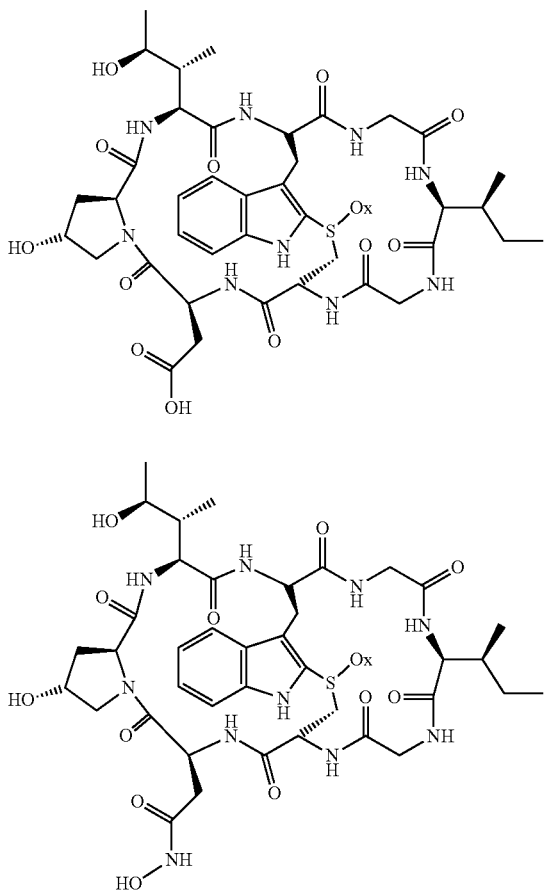

In a sixth aspect, the present invention relates to conjugates of γ-amaninamide (1; x=0, 1 or 2), γ-amaninamidic acid (2; x=0, 1 or 2), or γ-amaninamidic hydroxamic acid (3; x=0, 1 or 2) with a target-binding moiety, particularly wherein said target-binding moiety is an antibody or a fragment of an antibody comprising at least a functional antigen-binding domain, wherein said conjugate optionally comprises a linker moiety, which is connected on one side to a position or functional group present in said γ-amaninamide (1; x=0, 1 or 2), γ-amaninamidic acid (2; x=0, 1 or 2), or γ-amaninamidic hydroxamic acid (3; x=0, 1 or 2) and on another side with a position or functional group present in said target-binding moiety.

In a seventh aspect, the present invention relates to conjugates of γ-amaninamide (1; x=0, 1 or 2), γ-amaninamidic acid (2; x=0, 1 or 2), or γ-amaninamidic hydroxamic acid (3; x=0, 1 or 2) with a linking moiety, which is connected on one side to a position or functional group present in said γ-amaninamide (1; x=0, 1 or 2), γ-amaninamidic acid (2; x=0, 1 or 2), or γ-amaninamidic hydroxamic acid (3; x=0, 1 or 2) and which further comprises a position or functional group, which can directly or indirectly be connected to a position or functional group present in a target-binding moiety, particularly wherein said target-binding moiety is an antibody or a fragment of an antibody comprising at least a functional antigen-binding domain.

DETAILED DESCRIPTION OF THE INVENTION

Figure 1:
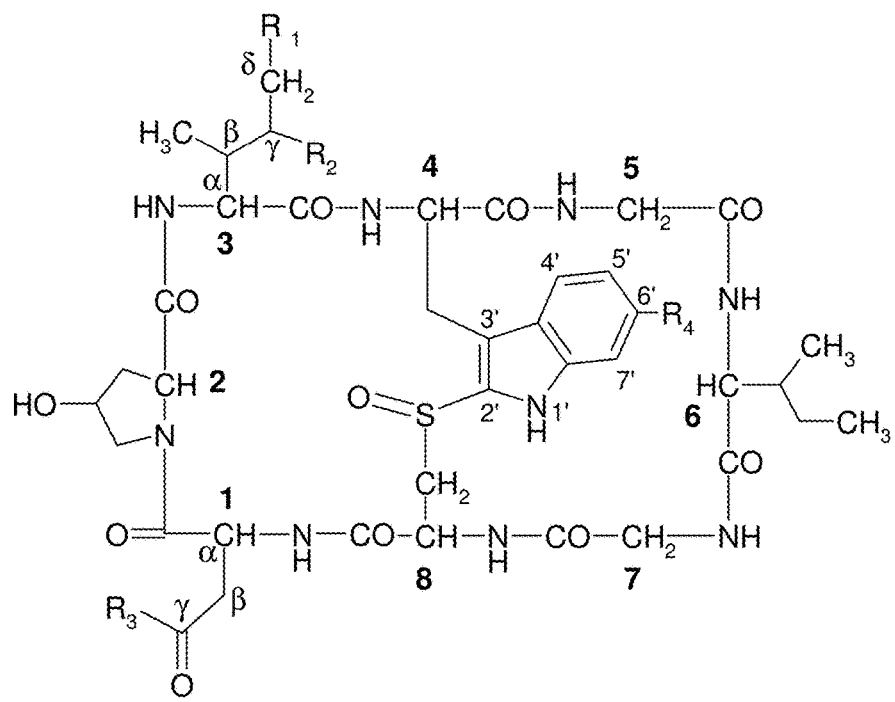
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer, composition or step or group of integers or steps, while any additional integer, composition or step or group of integers, compositions or steps may optionally be present as well, including embodiments, where no additional integer, composition or step or group of integers, compositions or steps are present. In such latter embodiments, the term "comprising" is used coterminous with "consisting of".

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present invention is based on the unexpected observation that readily available (2S,3R,4S)-L-4-hydroxyisoleucine (5)

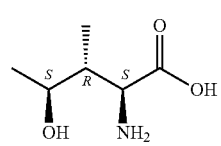

can be protected by an orthogonal protection strategy and can be used for the synthesis of amatoxins having γ-hydroxyisoleucine as amino acid 3.

Amino acid 3 of α-amanitin is γ,δ-dihydroxyisoleucine (CAS 55399-94-5), which is found in nature essentially only in α- and β-amanitin. Synthesis of γ,δ-dihydroxyisoleucine in the correct enantiomeric form is complicated and expensive.

In contrast, (2S,3R,4S)-L-4-hydroxyisoleucine (CAS 55399-93-4; structure 5) is found in fenugreek (*Trigonella foenum-graecum*) in large amounts (0.6% in dried seeds), which is commercially produced in hundreds of tons per year. As a consequence, compound 5 is commercially available.

Thus, in one aspect the present invention relates to a derivative of (2S,3R,4S)-L-4-hydroxyisoleucine (structure 5) having the structure (2S,3R,4S)—$CH_3$—$CH(OR^1)$—$CH(CH_3)$—$CH(NHR^2)$—$C(=O)OR^3$ (structure 6), wherein $R^1$ and $R^3$ are stable under conditions, where $R^2$ can be cleaved off, and $R^1$ and $R^2$ are stable under conditions, where $R^3$ can be cleaved off, in particular wherein $R^1$ is alkanoyl, particularly acetyl or $CH_3COCH_2CO$—, $R^2$ is Fmoc and $R^3$ is benzyl or t-butyl.

As used herein, a "chemical derivative" (or short: a "derivative") of a compound refers to a species having a chemical structure that is similar to the compound, yet containing at least one chemical group not present in the compound and/or deficient of at least one chemical group that is present in the compound. The compound to which the derivative is compared is known as the "parent" compound. Typically, a "derivative" may be produced from the parent compound in one or more chemical reaction steps.

So far, it had not yet been successful to use compound 5 for the synthesis of amatoxins, since compound 5 readily forms a lactone form (structure 9), which is no longer reactive.

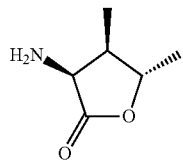

9

In particular embodiments, $R^2$ can be cleaved off by treatment with a base, particularly a secondary or tertiary amine, and $R^1$ and $R^3$ are stable under said conditions.

In particular such embodiments, $R^2$ is an Fmoc group. In particular such embodiments, the condition for selectively cleaving $R^2$ is selected from:
20% piperidine in DMF (1:4) for 3 to 5 minutes;
1 to 5% DBU/DMF;
20% piperidine and 1-5% DBU in DMF;
morpholine/DMF (1:1);
piperidine/DMF (1:4) at 45° C.;
0.1 M HOBt in piperidine/DMF (1:4);
$Bu_4N^+F^-$ in DMF and other tetraalkylammonium fluorides; and
2% HOBt, 2% hexamethyleneimine, 25% N-methylpyrrolidine in DMSO/NMP 1:1.

In particular embodiments, $R^3$ can be cleaved off by hydrogenation, and $R^1$ and $R^2$ are stable under said conditions.

In particular such embodiments, $R^3$ is a benzyl group. In particular such embodiments, the condition for selectively cleaving $R^3$ is hydrogenation with Pd/C (10%) at room temperature under normal pressure for 4 h.

In particular embodiments, $R^3$ can be cleaved off by mild acid treatment, and $R^1$ and $R^2$ are stable under said conditions.

In particular such embodiments, $R^3$ is a t-butyl group. In particular such embodiments, the condition for selectively cleaving $R^3$ is selected from treatment with HCl in acetic acid, or with trifluoroacetic acid.

In the context of the present invention, a group $R^x$ is stable under conditions, where another protecting group $R^y$ is cleaved off to more than 90%, particularly to more than 95%, when less than 10%, particularly less than 5% of said group $R^x$ are simultaneously cleaved off.

In a second aspect, the present invention relates to a method for synthesizing a compound of structure 6 (2S,3R,4S)—$CH_3$—$CH(OR^1)$—$CH(CH_3)$—$CH(NHR^2)$—$C(=O)OR^3$, comprising the steps of (a) complexing the compound of structure 5 with copper or boron, in particular with 9-borabicyclo [3,3,1]nonane (9-BBN); (b) acylation of the 4-hydroxy group with a compound $R^1$—$C(=O)$—$X$, wherein X is a leaving group, particularly wherein $R^1$ is alkyl, particularly $C_{1-6}$-alkyl, particularly methyl; (c) cleavage of the metal complex; (d) protection of the α-amino group with an $R^2$ group, particularly an Fmoc group; and (e) protection of the carboxyl group with an $R^3$ group, particularly a benzyl or t-butyl group. In particular embodiments, X is selected from Cl, Br, and —O—$C(=O)$—R.

In a third aspect, the present invention relates to a kit comprising a compound of structure 6, and at least one additional reagent for the synthesis of amatoxins or precursors thereof.

Scheme 1 (6*: structure 6 with $R^1$ = Me; $R^2$ = Fmoc; $R^3$ = benzyl):

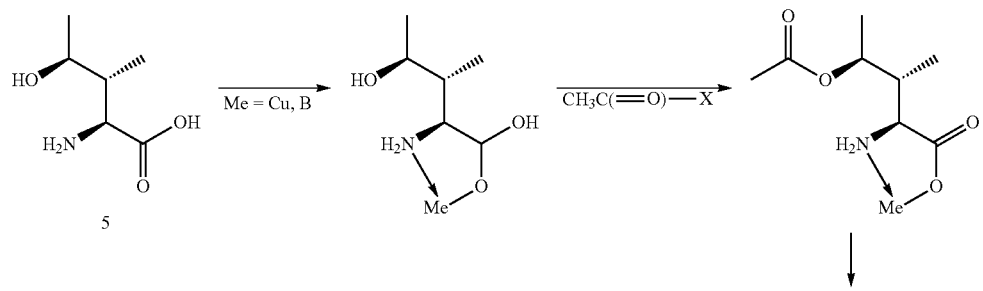

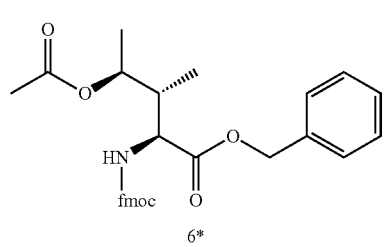
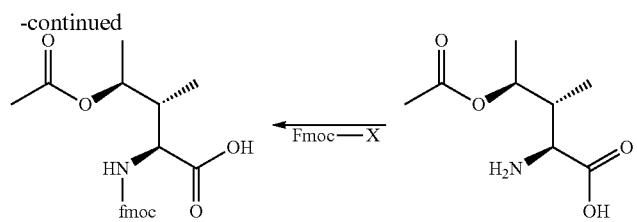

In the context of the present invention, the term "amatoxin" includes all cyclic peptides composed of 8 amino acids as isolated from the genus *Amanita* and described in Wieland, T. and Faulstich H. (Wieland T, Faulstich H., CRC Crit Rev Biochem. 5 (1978) 185-260), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in which the thioether sulfoxide moiety is replaced by a sulfide, sulfone, or by atoms different from sulfur, e.g. a carbon atom as in a carbaanalogue of amanitin, in each case wherein any such derivative or analogue is functionally active by inhibiting mammalian RNA polymerase II.

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined above. Amatoxins which are particularly suitable for the conjugates of the present invention are α-amanitin, β-amanitin, γ-amanitin, ε-amanitin, amanin, amaninamide, amanullin, amanullinic acid, γ-amanin, and γ-amaninamide as shown in FIG. 1 as well as salts, chemical derivatives, semisynthetic analogues, and synthetic analogues thereof. Particularly preferred amatoxins for use in the present invention are γ-amanin, γ-amaninamide γ-amanitin, and ε-amanitin, particularly γ-amanin and γ-amaninamide.

In the context of the present invention, the term "additional reagent for the synthesis of amatoxins or precursors thereof" in particular includes any reagent selected from (i) appropriately protected and/or activated amino acid-based compounds corresponding to any one of the remaining seven amino acids forming the eight amino acid backbone structure of amatoxins, including amino acids coupled to solid supports; (ii) appropriately protected and/or activated preformed di- or polypeptide building blocks corresponding to parts of eight amino acid backbone structure of amatoxins, including such building blocks coupled to solid supports; and (iii) ancillary reagents required for activating, deprotecting, coupling, synthesizing and/or modifying reagents according to (i) or (ii) or products obtained from the reaction of compound 6 with any of the reagents according to (i) or (ii).

In particular embodiments, said at least one additional reagent is selected from the list of:
(i) a resin, particularly a resin selected from the group of: a Merrifield resin; a Rink-Amid resin; and a THP-resin;

(ii) a protected hydroxyproline, particularly fluorenylmethyloxycarbonyl-(Fmoc-)-protected O-allyl hydroxyproline (FmocHypOAll);

(iii) a protected asparagine, particularly Fmoc-protected N-trityl asparagine (Fmoc(N-Tri)AsnOH);

(iv) a protected Cys-Trp dipeptide, particularly Fmoc-protected Cys-Trp dipeptide with —SH and —OH protection groups (FmocCys(S-2-((o-NO$_2$Ph)SO$_2$Trp-O-Allyl))]OH);

(v) a protected glycine, particularly Fmoc-protected glycine (FmocGly);

(vi) a protected isoleucine, particularly Fmoc-protected isoleucine (FmocIle);

(vii) a peptide coupling reagent, particularly a peptide coupling reagent selected from the group of: O-(benzotriazol-1-yl)-N,N,N',N'-tetramethyluronium tetrafluoroborate (TBTU); benzotriazol-1-yl-oxytripyrrolidinophosphonium hexafluorophosphate (PyBOP); and o-(7-azabenzotriazol-1-yl)-N,N,N',N'-tetramethyluronium hexafluorophosphate (HATU); and (viii) a tertiary amine, particularly N,N-diisopropylethylamine (DiPEA).

In a fourth aspect, the present invention relates to a method for synthesizing an amatoxin, or precursor molecule therefor, comprising the steps of (a1) cleaving protection group R$^2$ from a compound of structure 6, and (a2) coupling of the deprotected variant of 6 with a free amino group obtained according to step (a1) to an activated variant of hydroxyproline, a protected variant thereof or synthon therefor, particularly to a compound of structure selected from 7, 8 and L, wherein L is a hydroxyproline-preloaded resin, for example a tetrahydropyranyl (THP) resin.

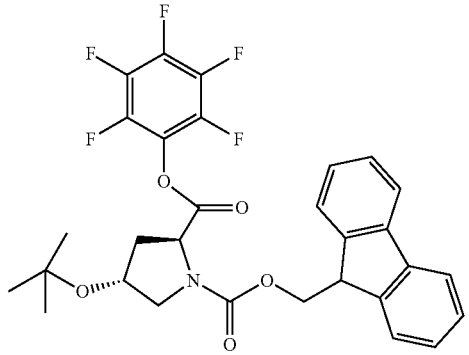

-continued

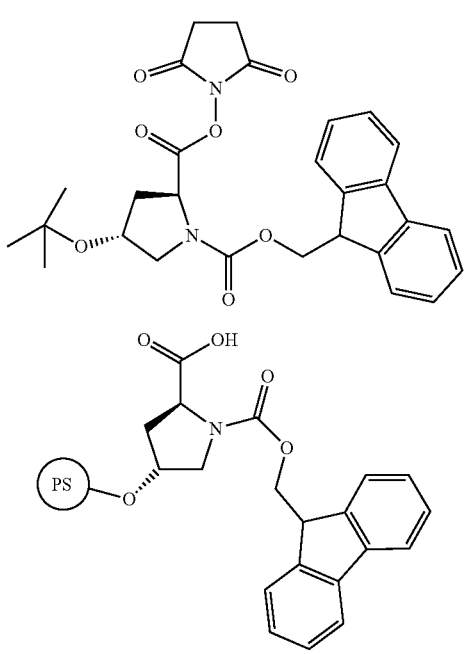

8

L

In the context of the present invention, the term "synthon" refers to a compound that is, or can be used as, a synthetic equivalent for a particular compound of interest in a chemical reaction. This definition includes compounds, where a moiety of the compound of interest that would be labile or reactive under the conditions to be used in said chemical reaction is protected or masked by an appropriate protection group that can be cleaved off after said chemical reaction.

Figure 2:
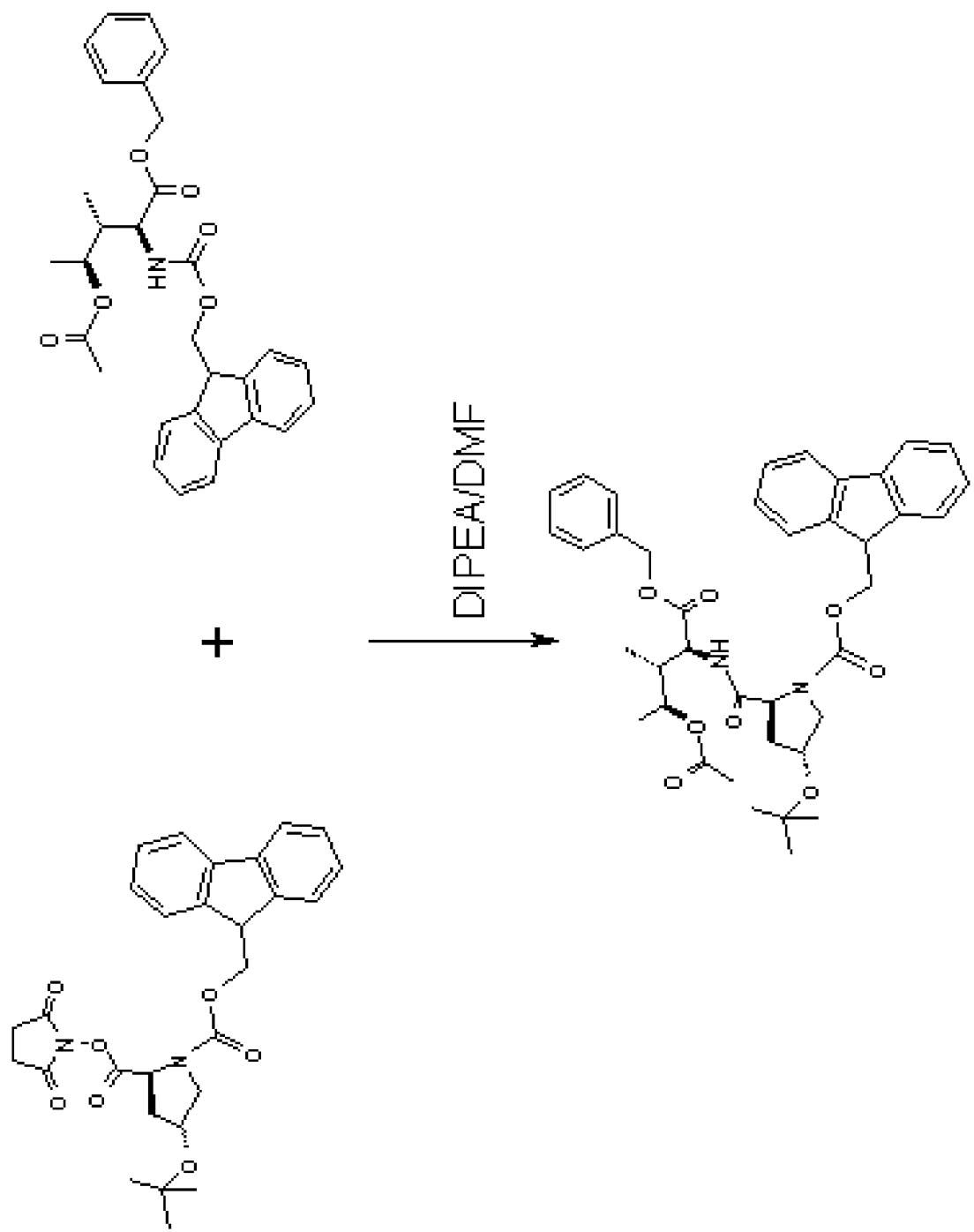
FIG. 2 shows the synthesis scheme (steps (a) to (g)) for compound 1.
Figure 2:
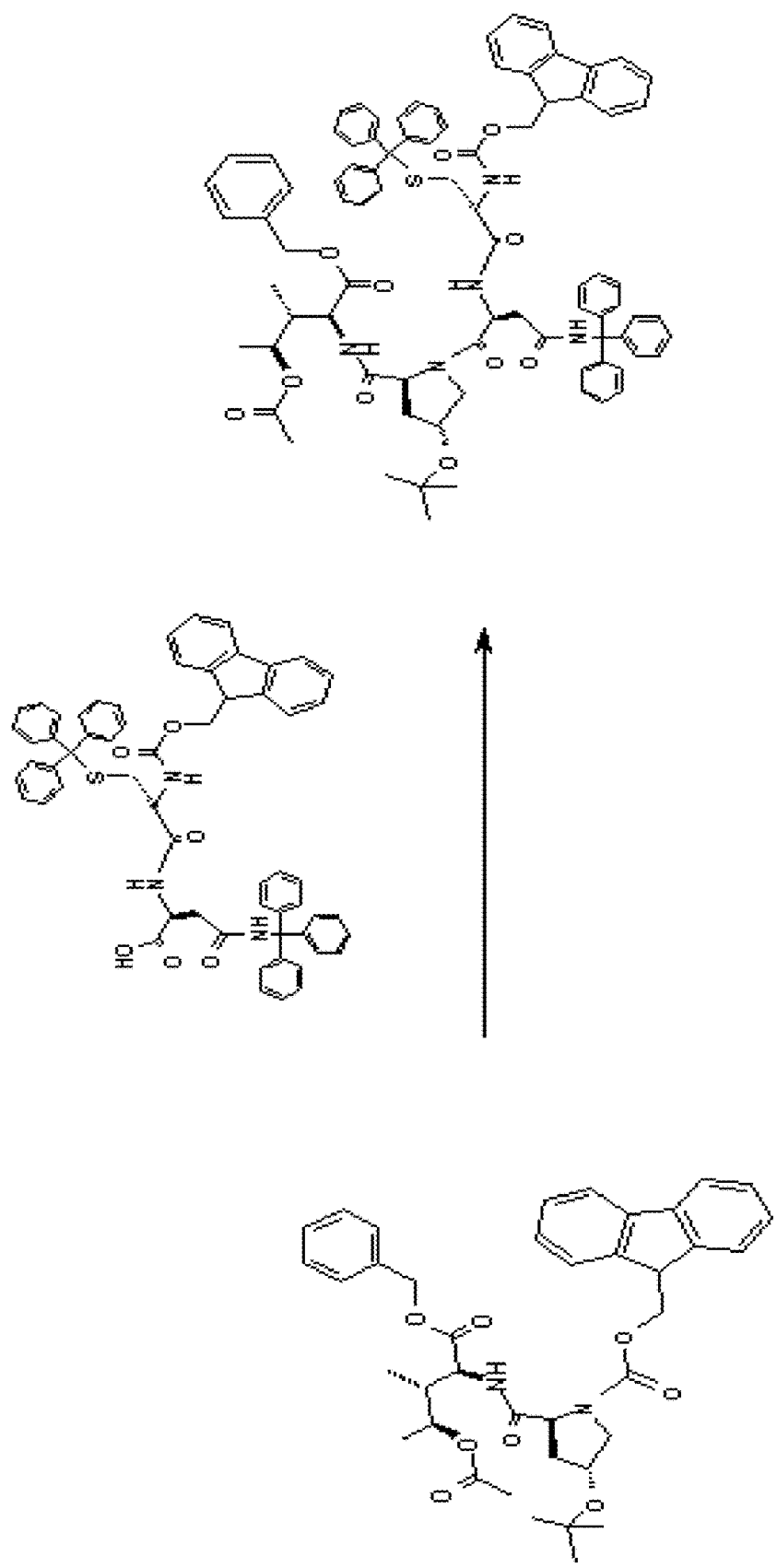
Figure 2:
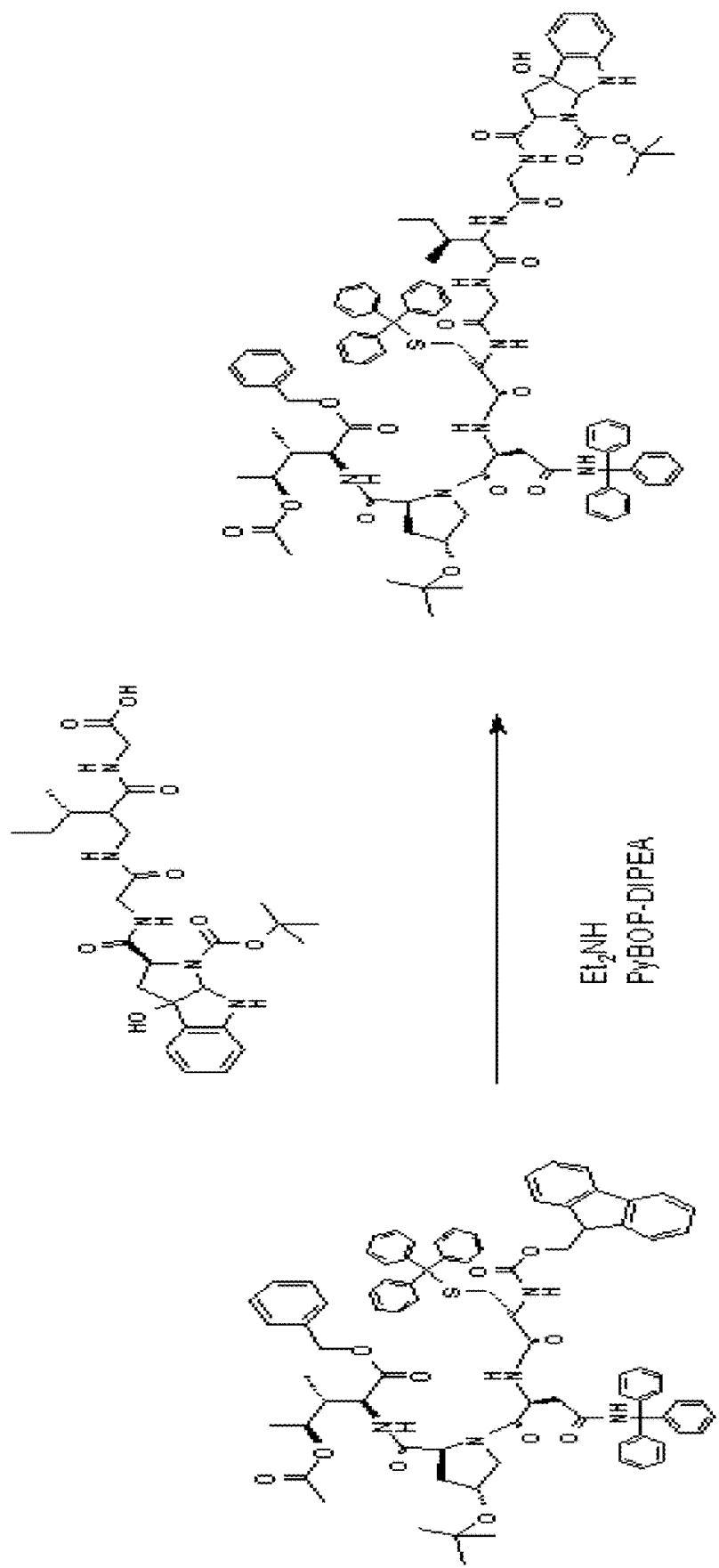
Figure 2:
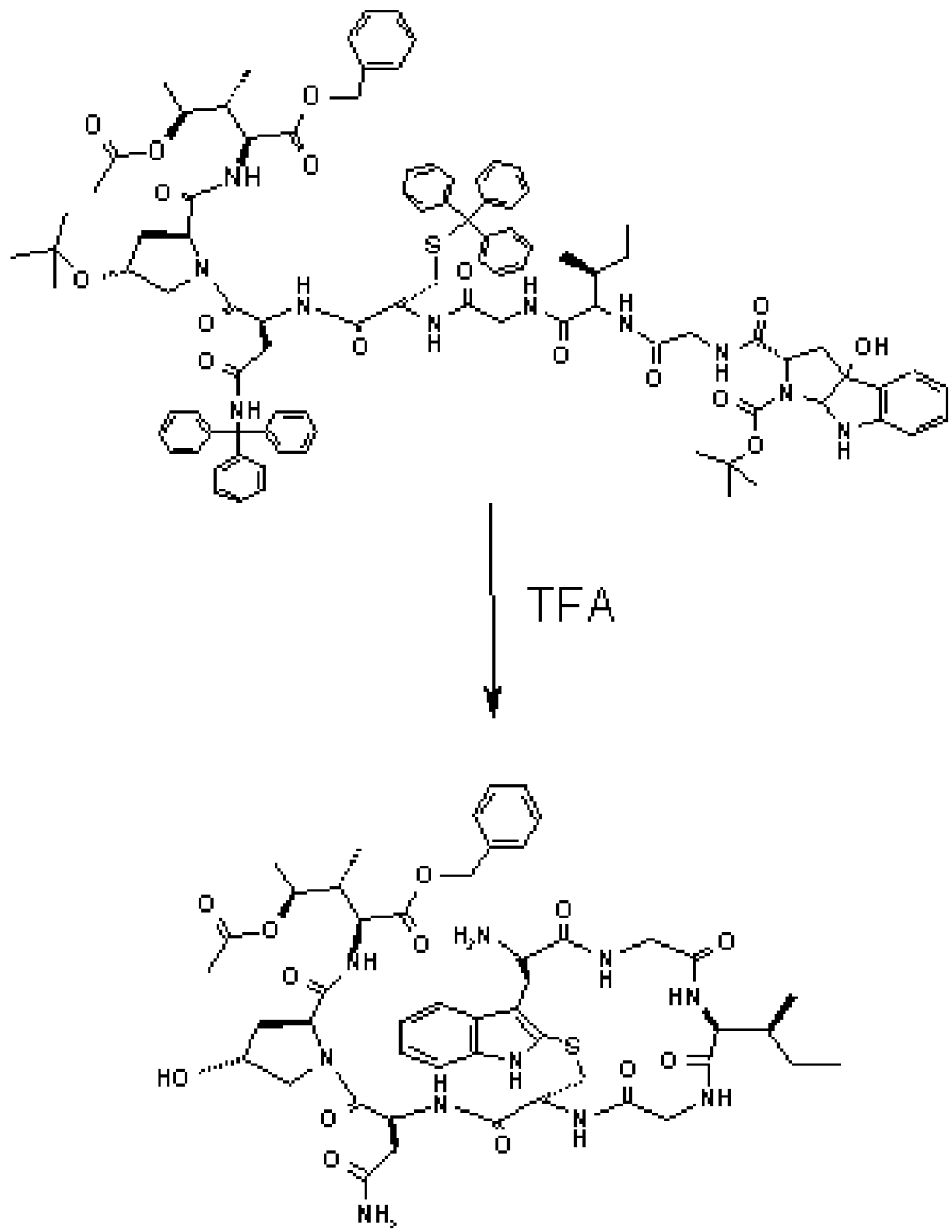
Figure 2:
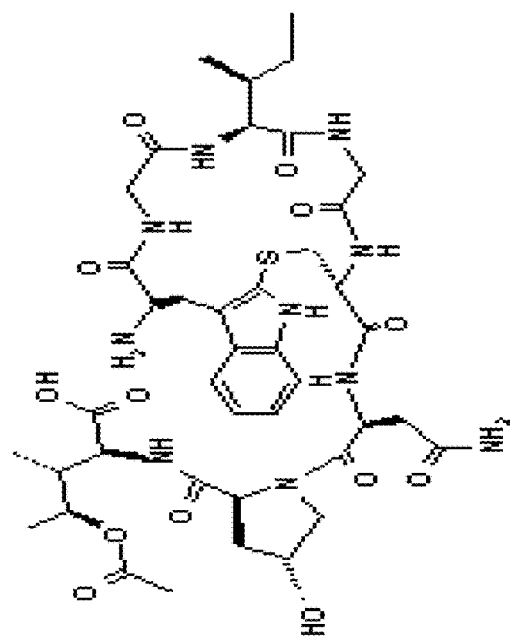
Figure 2:
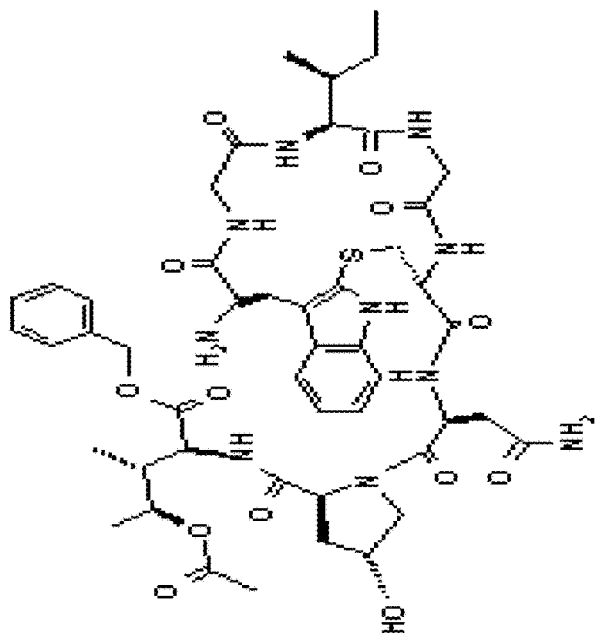
Figure 2:
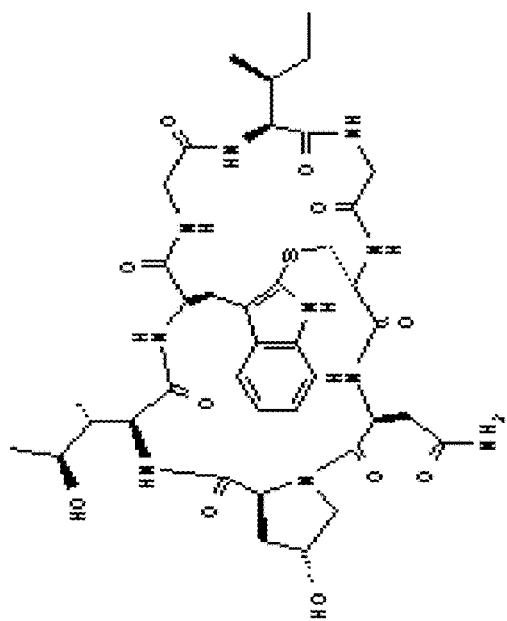
Figure 2:
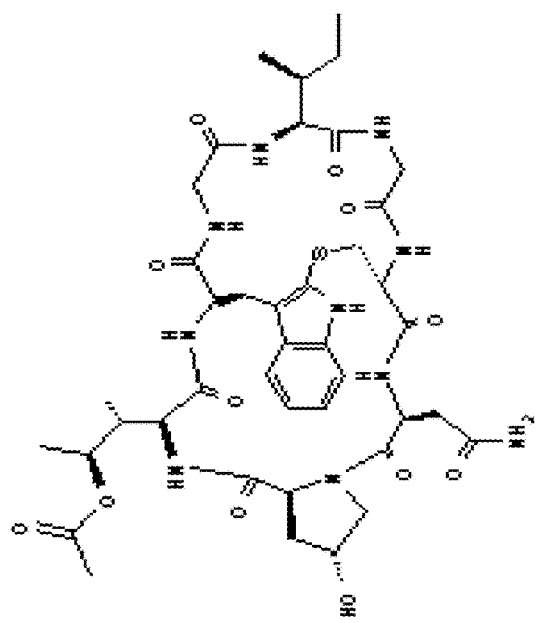
Figure 3:
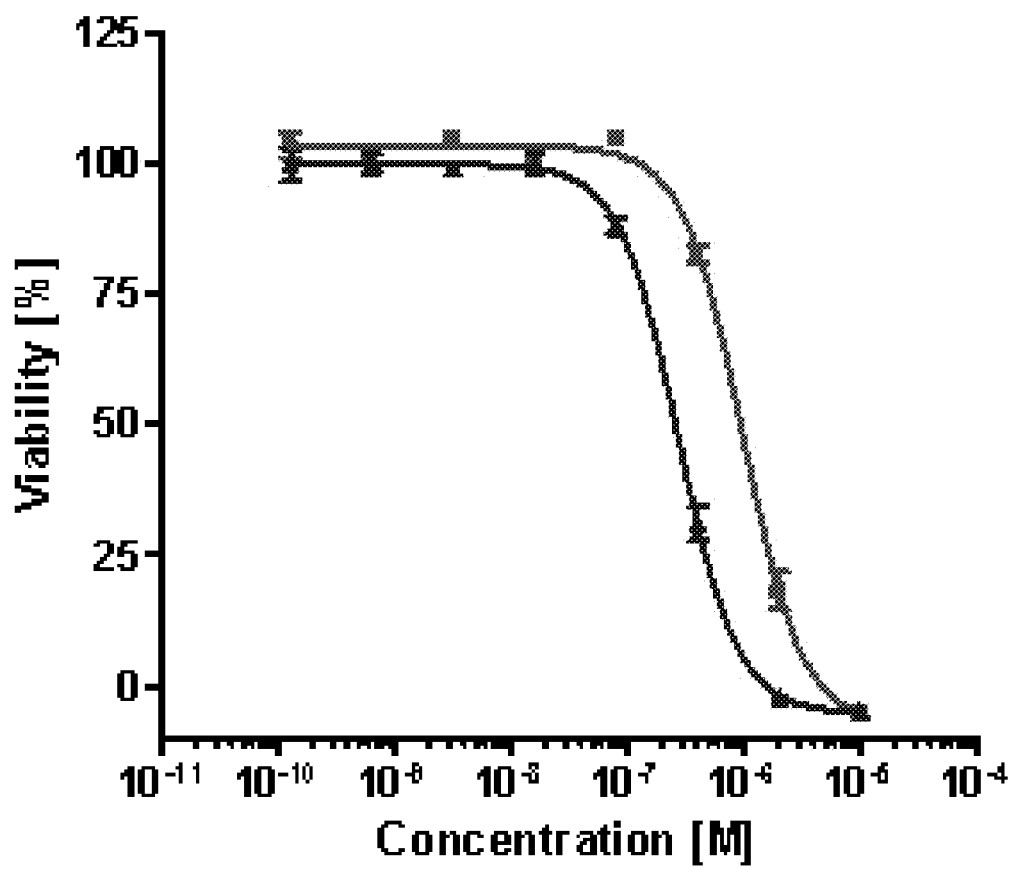
FIG. 3 shows the viability of SKOV3 cells treated with ■: γ-amaninamide (1) (EC50: 9.7 $10^{-7}$ M); ▲: γ-amanitin (4) (EC50: 2.7 $10^{-7}$ M).
Figure 4:
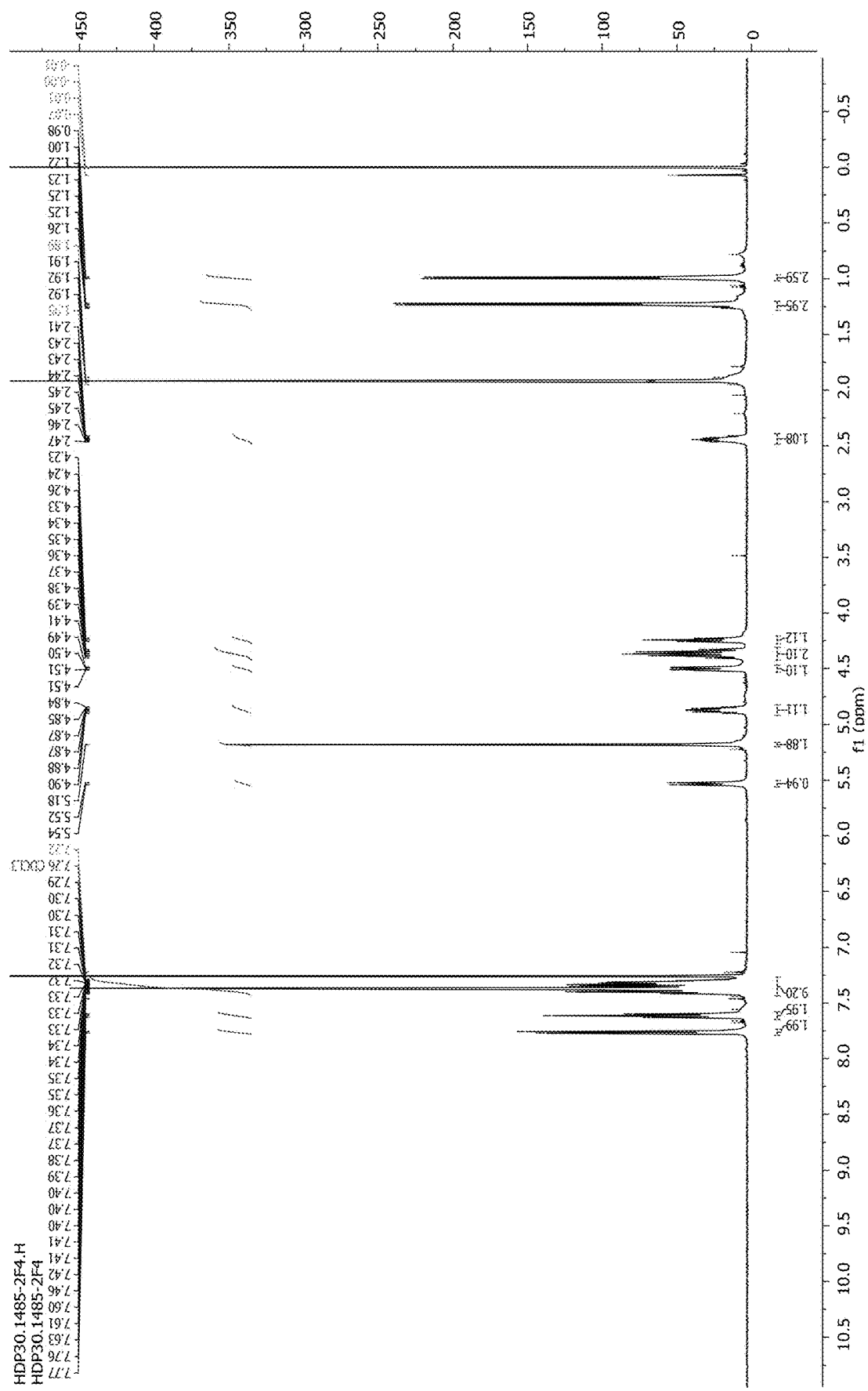
FIG. 4 shows NMR spectra for compound HDP 30.1485: (a) $^{1}$H NMR (500 MHz, Chloroform-d); (b) $^{13}$C NMR (126 MHz, CDCl$_{3}$).
Figure 4:
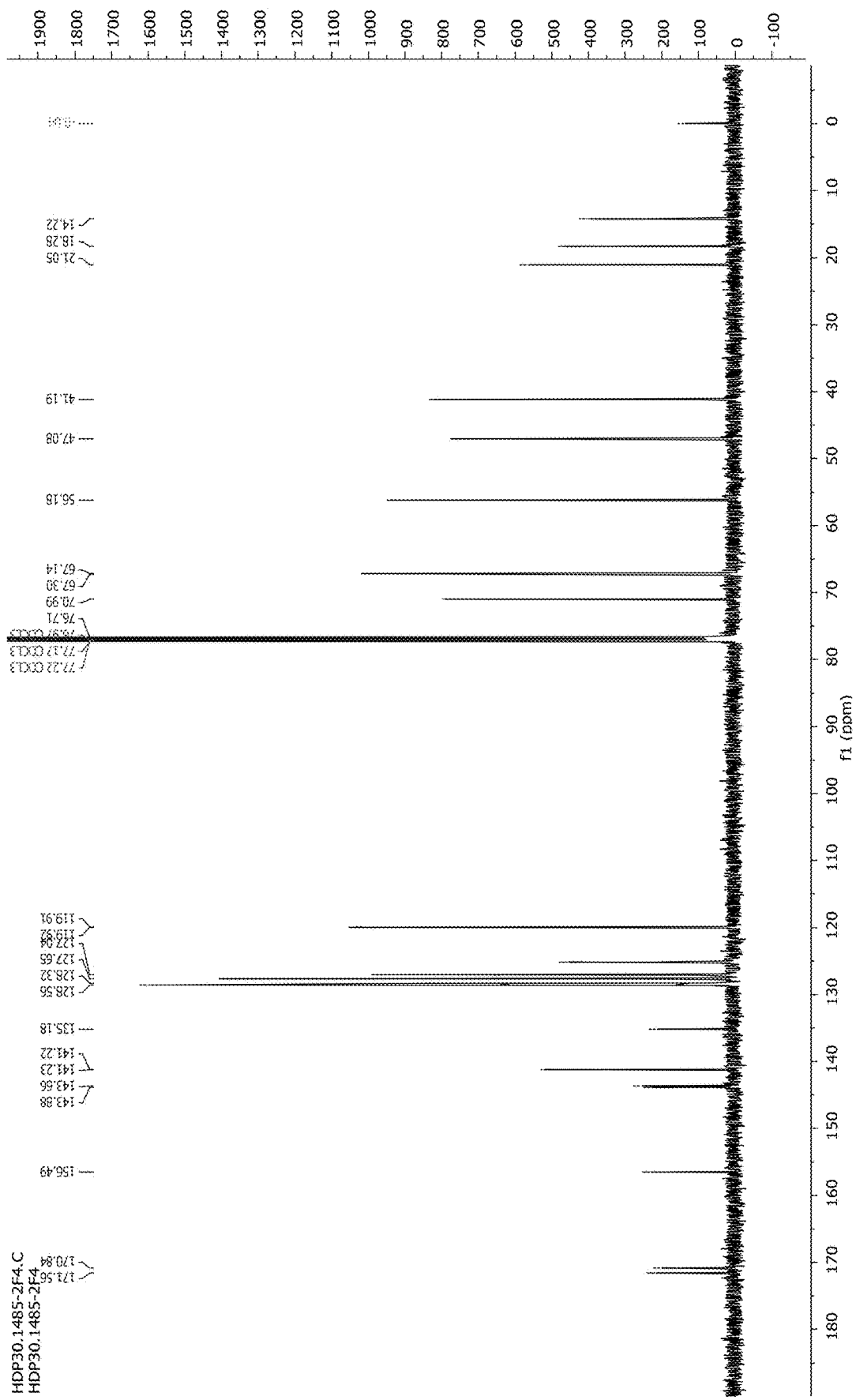

In particular embodiments of that aspect of the invention, the method further comprises one or more of steps (b) to (g) as shown in FIG. 2.

In particular embodiments, the remaining amino acids are coupled by a N-terminal synthetic strategy.

In particular embodiments, the method is a solid-phase based synthesis additionally comprising the steps:

(b) iterative Fmoc N-deprotection and coupling of G (obtained in step (a) from reaction of compound 6 with resin L) with Fmoc-(N-Tri)Asn-OH; FmocCys(S-2-((o-NO$_2$Ph)SO$_2$Trp-O-Allyl))]OH, Fmoc-Gly-OH, Fmoc-Ile-OH, Fmoc-Gly-OH to create compound H:

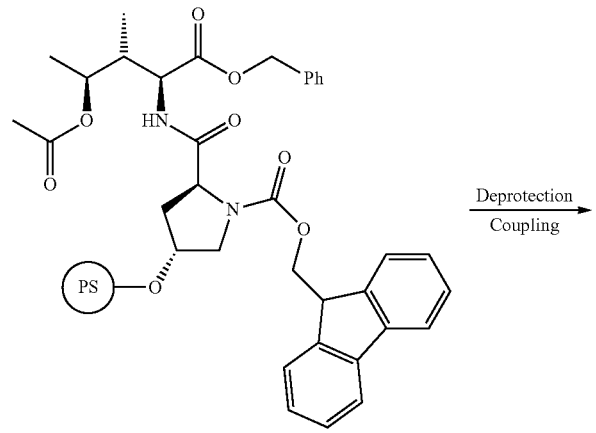

G

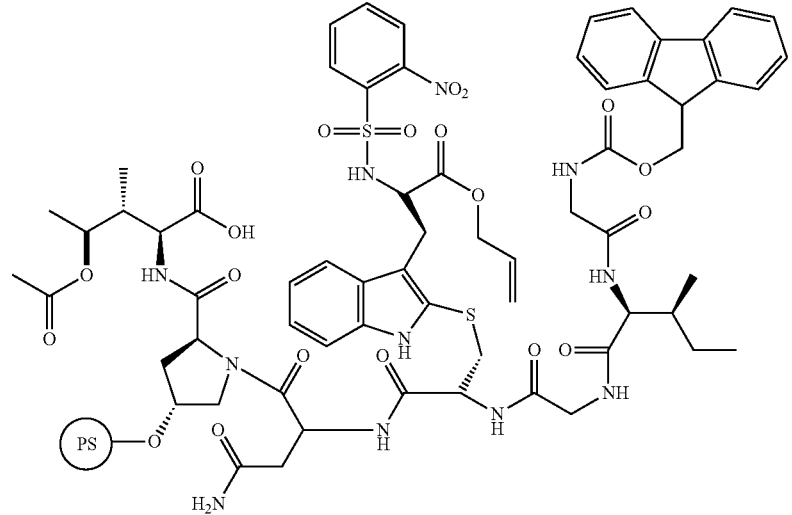

H (c) O-allyl- and N-Fmoc deprotection of H followed by cyclisation to create compound I (B-ring closure):
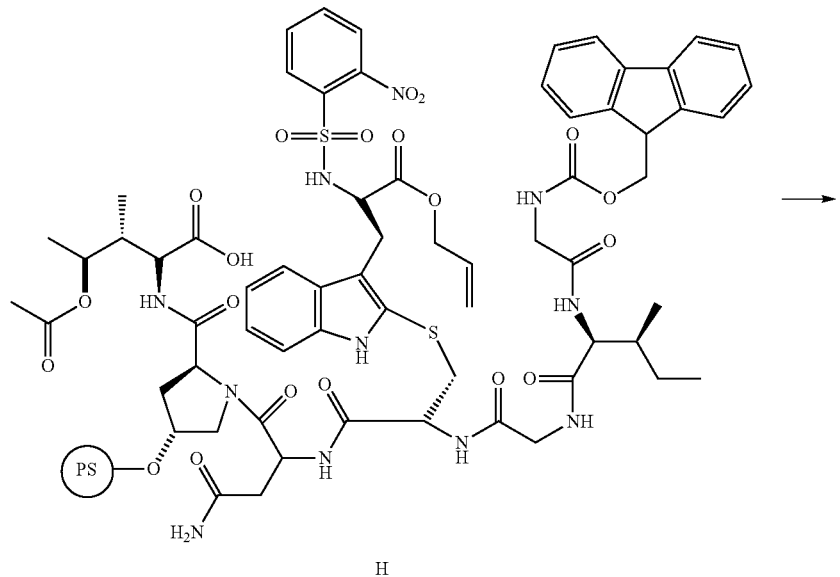
(d) 2-nitro aryl sulfonamide N-deprotection and secession of I from resin to create compound J:

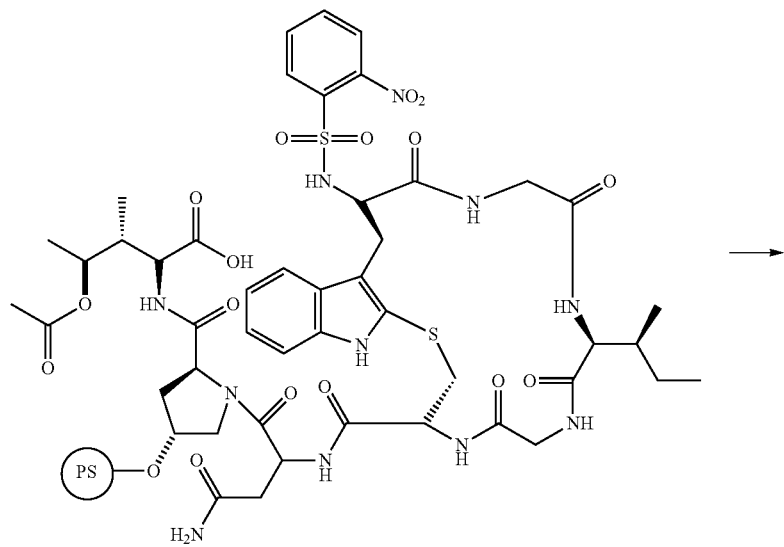
I
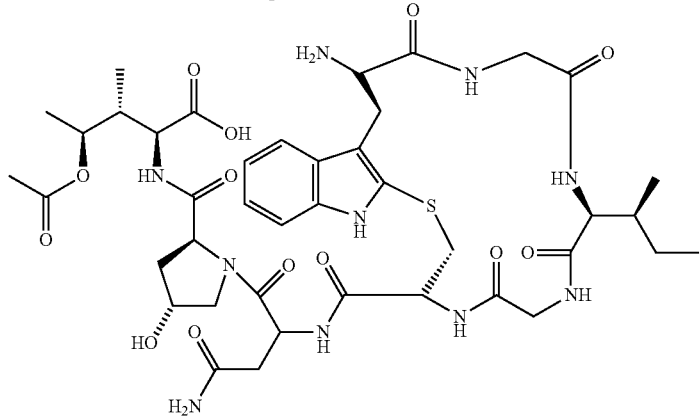
J
(e) solution phase cyclisation of J creating γ-amaninamide derivative K:
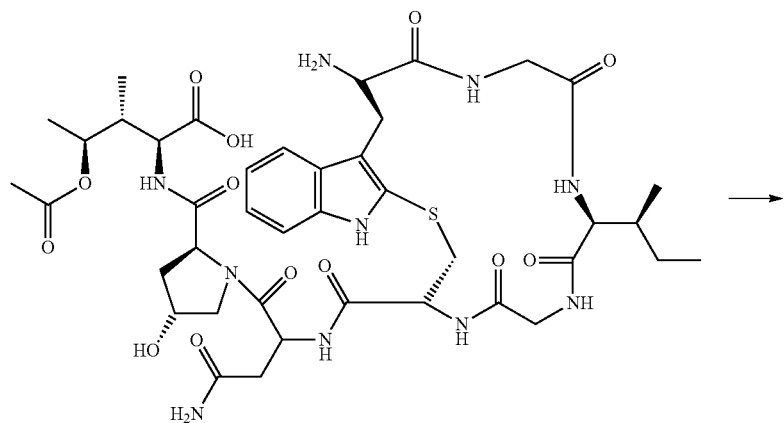
J

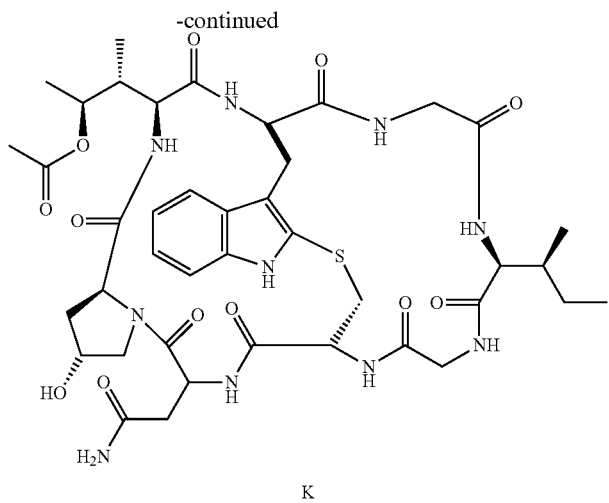

K

In yet another aspect, the present invention relates to a method for synthesizing γ-amaninamide (1; x=0, 1 or 2), γ-amaninamidic acid (2; x=0, 1 or 2), and γ-amaninamidic hydroxamic acid (3; x=0, 1 or 2) or a derivative thereof, or precursor molecule therefor, in solution.

In a particular embodiment, x is selected from 1 and 2, and in particular is 1.

In certain embodiments, such method additionally comprises one or more of the following steps:

(b) iterative Fmoc N-deprotection and coupling of M (obtained in step (a) from reaction of compound 6 with compound 7 or compound 8) with Fmoc-(N-Tri)Asn-OH; Fmoc-(S-Tri)Cys-OH, Fmoc-Gly-OH, Fmoc-Ile-OH, Fmoc-Gly-OH and N-Boc-HPIOH[1] [[1] Zanotti, Giancarlo; Birr Christian; Wieland Theodor; International Journal of Peptide & Protein Research 18 (1981) 162-8] to create compound N;

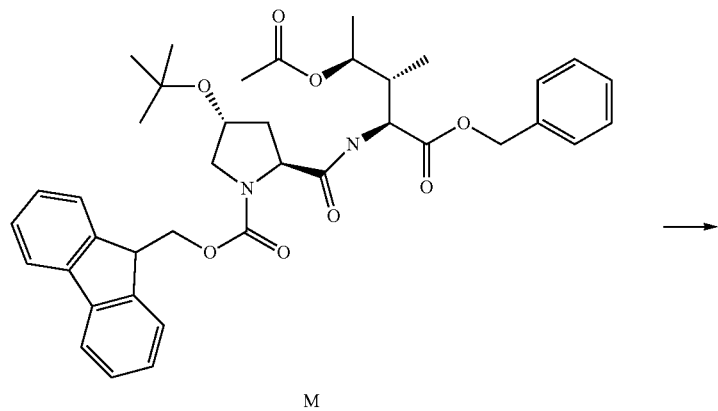

M

-continued

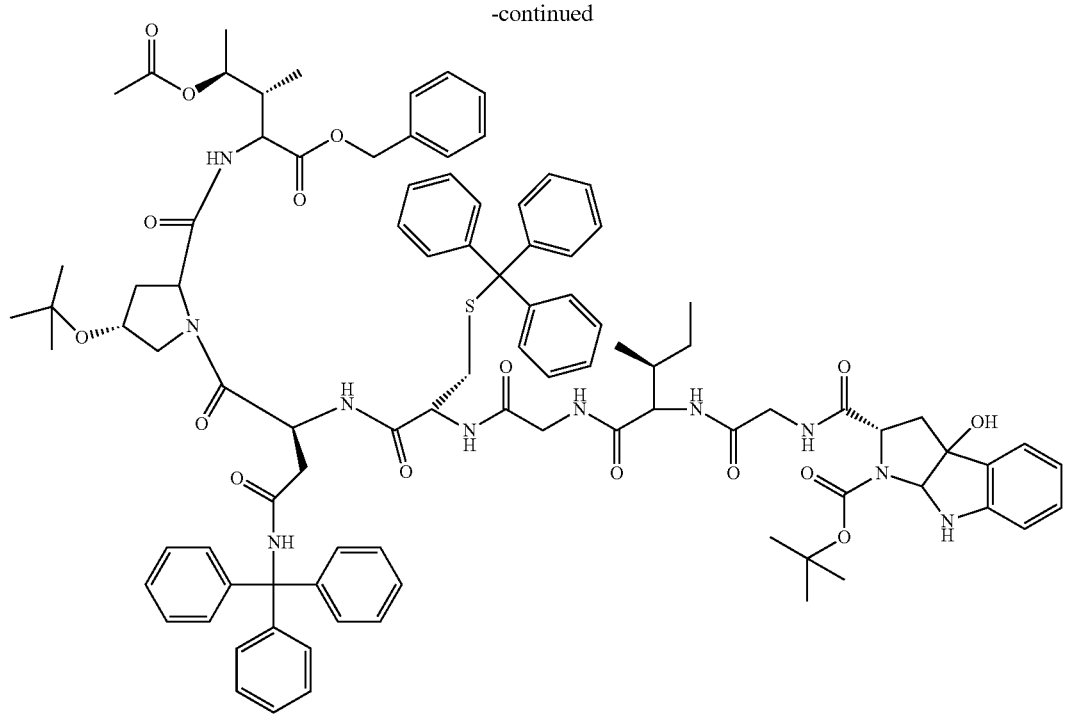

(c) acidic deprotection of N- and S-trityl, O-tert-butyl and N-tertbutyloxycarbonyl protection groups and in situ ring closure by a Savige-Fontana reaction (Savige & Fontana, Int J Pept Protein Res. 15 (1980) 102-12) yielding compound J.

In a fifth aspect, the present invention relates to γ-amaninamide (1; x=0, 1 or 2), γ-amaninamidic acid (2; x=0, 1 or 2), and γ-amaninamidic hydroxamic acid (3; x=0, 1 or 2).

-continued

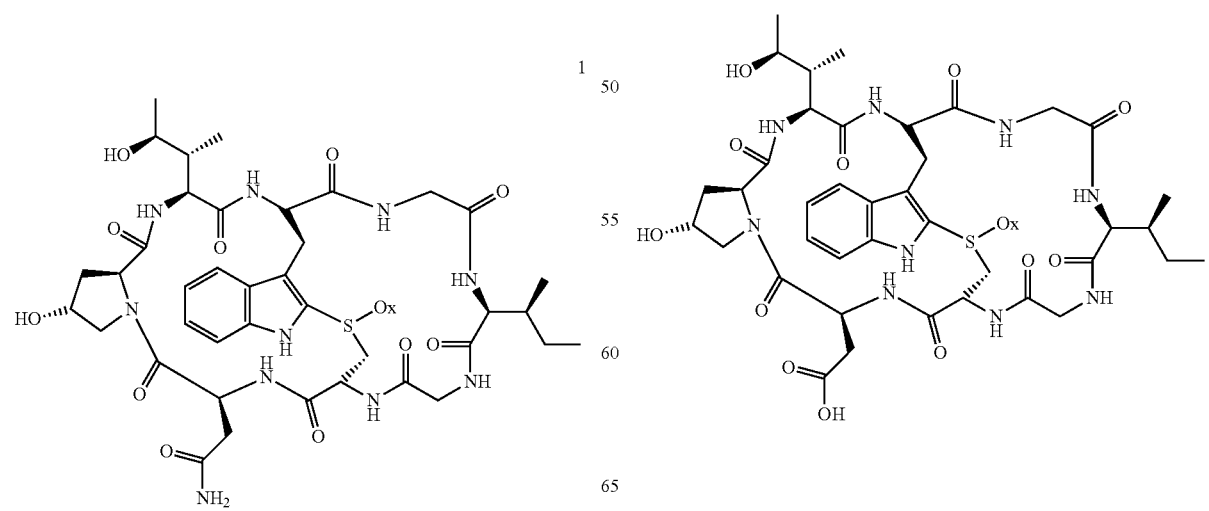

-continued

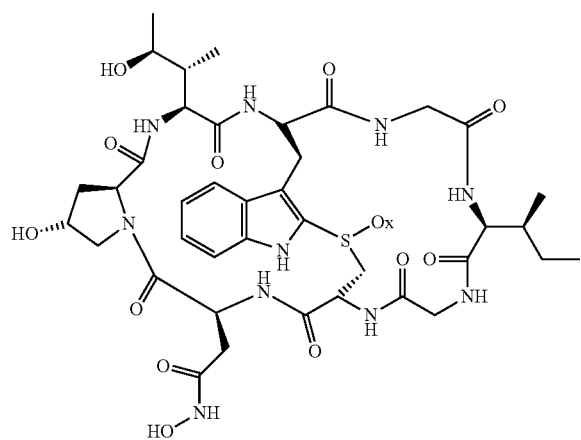
3

In a particular embodiment, x is selected from 1 and 2, and in particular is 1.

In a particular embodiment, compound 1, 2 or 3 has a purity greater than 90%, particularly greater than 95%.

In the context of the present invention, the term "purity" refers to the total amount of compound 1, 2 or 3 being present. A purity of greater than 90%, for example, means that in 1 mg of a composition comprising compound 1, there are more than 90%, i.e. more than 900 μg, of compound 1. The remaining part, i.e. the impurities may include unreacted starting material and other reactants, solvents, cleavage products and/or side products.

In a particular embodiment, a composition comprising a compound selected from compound 1, 2 or 3 with a purity greater than 90% comprises more than 100 mg of compound 1, 2 or 3, respectively. Thus, trace amount of compounds 1, 2 or 3 that arguably may be present in complex naturally occurring amatoxin mixtures, e.g. from mushroom extracts, or in complex synthetic mixtures, e.g. as side products, are explicitly excluded.

In a sixth aspect, the present invention relates to conjugates of γ-amaninamide (1; x=0, 1 or 2), γ-amaninamidic acid (2; x=0, 1 or 2), or γ-amaninamidic hydroxamic acid (3; x=0, 1 or 2) with a target-binding moiety, particularly wherein said target-binding moiety is an antibody or antigen-binding fragments thereof, wherein said conjugate optionally comprises a linker moiety, which is connected on one side to a position or functional group present in said γ-amaninamide (1; x=0, 1 or 2), γ-amaninamidic acid (2; x=0, 1 or 2), or γ-amaninamidic hydroxamic acid (3; x=0, 1 or 2) and on another side with a position or functional group present in said target-binding moiety.

In a particular embodiment, x is selected from 1 and 2, and in particular is 1.

The term "target-binding moiety", as used herein, refers to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers. "Target-binding moieties" suitable for use in the present invention typically have a molecular mass of 40 000 Da (40 kDa) or more.

As used herein, a first compound (e.g. an antibody) is considered to "specifically bind" to a second compound (e.g. an antigen, such as a target protein), if it has a dissociation constant $K_D$ to said second compound of 100 μM or less, preferably 50 μM or less, preferably 30 μM or less, preferably 20 μM or less, preferably 10 μM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

In the context of the present application the terms "target molecule" and "target epitope", respectively, refers to an antigen and an epitope of an antigen, respectively, that is specifically bound by a target-binding moiety. Preferably the target molecule is a tumour-associated antigen, in particular an antigen or an epitope which is present on the surface of one or more tumour cell types in an increased concentration and/or in a different steric configuration as compared to the surface of non-tumour cells Preferably, said antigen or epitope is present on the surface of one or more tumour cell types, but not on the surface of non-tumour cells. In particular embodiments, the target-binding moiety specifically binds to an epitope of HER-2/neu or epithelial cell adhesion molecule (EpCAM). In other embodiments, said antigen or epitope is preferentially expressed on cells involved in autoimmune diseases. In particular such embodiments, the target-binding moiety specifically binds to an epitope of the IL-6 receptor (IL-6R).

The term "antibody or antigen binding fragment thereof", as used herein, refers to immunoglobulin molecules and immunologically active portions of immunoglobulin molecules, i.e. molecules that contain an antigen-binding site that immunospecifically binds an antigen. Thus, the term "antigen-binding fragments thereof" refers to a fragment of an antibody comprising at least a functional antigen-binding domain. Also comprised are immunoglobulin-like proteins that are selected through techniques including, for example, phage display to specifically bind to a target molecule, e.g. to the target protein Her-2/neu or EpCAM. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. "Antibodies and antigen-binding fragments thereof" suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, F(ab')$_2$ fragments, fragments produced by a Fab expression library, diabodies or tetrabodies (Holliger P. et al., Proc Natl Acad Sci USA. 90 (1993) 6444-8), nanobodies, anti-idiotypic (anti-Id) antibodies (including, e.g., anti-Id antibodies to antibodies of the invention), and epitope-binding fragments of any of the above.

In some embodiments the antigen-binding fragments are human antigen-binding antibody fragments of the present invention and include, but are not limited to, Fab, Fab' and F(ab')$_2$, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also included in the invention are antigen-binding fragments also comprising any combination of variable domain(s) with a hinge region, CL, CH1, CH2, and CH3 domains.

Antibodies usable in the invention may be from any animal origin including birds and mammals. Preferably, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz et al., Nat Biotechnol. 2005, 1257-68). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins.

The term "nucleic acid aptamer" refers to a nucleic acid molecule that has been engineered through repeated rounds of in vitro selection or SELEX (systematic evolution of ligands by exponential enrichment) to bind to a target molecule (for a review see: Brody and Gold, J Biotechnol. 74 (2000) 5-13). The nucleic acid aptamer may be a DNA or RNA molecule. The aptamers may contain modifications, e.g. modified nucleotides such as 2'-fluorine-substituted pyrimidines.

A "linker" in the context of the present invention refers to a structure that is connecting two components, each being attached to one end of the linker. In the case of the linker being a bond, a direct linkage of amatoxin to the antibody may decrease the ability of the amatoxin to interact with RNA polymerase II. In particular embodiments, the linker increases the distance between two components and alleviates steric interference between these components, such as in the present case between the antibody and the amatoxin. In particular embodiments, the linker has a continuous chain of between 1 and 30 atoms (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms) in its backbone, i.e. the length of the linker is defined as the shortest connection as measured by the number of atoms or bonds between the amatoxin moiety and the antibody, wherein one side of the linker backbone has been reacted with the amatoxin and, the other side is available for reaction, or has been reacted, with an antibody. In the context of the present invention, a linker preferably is a $C_{1-20}$-alkylene, $C_{1-20}$-heteroalkylene, $C_{2-20}$-alkenylene, $C_{2-20}$-heteroalkenylene, $C_{2-20}$-alkynylene, $C_{2-20}$-heteroalkynylene, cycloalkylene, heterocycloalkylene, arylene, heteroarylene, aralkylene, or a heteroaralkylene group, optionally substituted. The linker may contain one or more structural elements such as carboxamide, ester, ether, thioether, disulfide, urea, thiourea, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the antibody. To that end the linker to be will carry two groups, preferably at a proximal and distal end, which can (i) form a covalent bond to a group present in one of the components to be linked, preferably an activated group on an amatoxin or the target binding-peptide or (ii) which is or can be activated to form a covalent bond with a group on an amatoxin. Accordingly, it is preferred that chemical groups are at the distal and proximal end of the linker, which are the result of such a coupling reaction, e.g. an ester, an ether, a urethane, a peptide bond etc.

In particular embodiments, the linker L is a linear chain of between 1 and 20 atoms independently selected from C, O, N and S, particularly between 2 and 18 atoms, more particularly between 5 and 16 atoms, and even more particularly between 6 and 15 atoms. In particular embodiments, at least 60% of the atoms in the linear chain are C atoms. In particular embodiments, the atoms in the linear chain are linked by single bonds.

In particular embodiments. the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, comprising from 1 to 4 heteroatoms selected from N, O, and S, wherein said linker is optionally substituted.

The term "alkylene" refers to a bivalent straight chain saturated hydrocarbon groups having from 1 to 20 carbon atoms, including groups having from 1 to 10 carbon atoms. In certain embodiments, alkylene groups may be lower alkylene groups. The term "lower alkylene" refers to alkylene groups having from 1 to 6 carbon atoms, and in certain embodiments from 1 to 5 or 1 to 4 carbon atoms. Examples of alkylene groups include, but are not limited to, methylene ($—CH_2—$), ethylene ($—CH_2—CH_2—$), n-propylene, n-butylene, n-pentylene, and n-hexylene.

The term "alkenylene" refers to bivalent straight chain groups having 2 to 20 carbon atoms, wherein at least one of the carbon-carbon bonds is a double bond, while other bonds may be single bonds or further double bonds. The term "alkynylene" herein refers to groups having 2 to 20 carbon atoms, wherein at least one of the carbon-carbon bonds is a triple bond, while other bonds may be single, double or further triple bonds. Examples of alkenylene groups include ethenylene ($—CH{=}CH—$), 1-propenylene, 2-propenylene, 1-butenylene, 2-butenylene, 3-butenylene, and the like. Examples of alkynylene groups include ethynylene, 1-propynylene, 2-propynylene, and so forth.

As used herein, "cycloalkylene" is intended to refer to a bivalent ring being part of any stable monocyclic or polycyclic system, where such ring has between 3 and 12 carbon atoms, but no heteroatom, and where such ring is fully saturated, and the term "cycloalkenylene" is intended to refer to a bivalent ring being part of any stable monocyclic or polycyclic system, where such ring has between 3 and 12 carbon atoms, but no heteroatom, and where such ring is at least partially unsaturated (but excluding any arylene ring).

Examples of cycloalkylenes include, but are not limited to, cyclopropylene, cyclobutylene, cyclopentylene, cyclohexylene, and cycloheptylene. Examples of cycloalkenylenes include, but are not limited to, cyclopentenylene and cyclohexenylene.

As used herein, the terms "heterocycloalkylene" and "heterocycloalkenylene" are intended to refer to a bivalent ring being part of any stable monocyclic or polycyclic ring system, where such ring has between 3 and about 12 atoms, and where such ring consists of carbon atoms and at least one heteroatom, particularly at least one heteroatom independently selected from the group consisting of N, O and S, with heterocycloalkylene referring to such a ring that is fully saturated, and heterocycloalkenylene referring to a ring that is at least partially unsaturated (but excluding any arylene or heteroarylene ring).

The term "arylene" is intended to mean a bivalent ring or ring system being part of any stable monocyclic or polycyclic system, where such ring or ring system has between 3 and 20 carbon atoms, but has no heteroatom, which ring or ring system consists of an aromatic moiety as defined by the "4n+2" π electron rule, including phenylene.

As used herein, the term "heteroarylene" refers to a bivalent ring or ring system being part of any stable mono- or polycyclic system, where such ring or ring system has between 3 and 20 atoms, which ring or ring system consists of an aromatic moiety as defined by the "4n+2" π electron rule and contains carbon atoms and one or more nitrogen, sulfur, and/or oxygen heteroatoms.

In the context of the present invention, the term "substituted" is intended to indicate that one or more hydrogens present in the backbone of a linker is replaced with a selection from the indicated group(s), provided that the indicated atom's normal valency, or that of the appropriate atom of the group that is substituted, is not exceeded, and that the substitution results in a stable compound. The term "optionally substituted" is intended to mean that the linker is either unsubstituted or substituted, as defined herein, with one or more substituents, as defined herein. When a substituent is a keto (or oxo, i.e. =O) group, a thio or imino group or the like, then two hydrogens on the linker backbone atom are replaced. Exemplary substituents include, for example, alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio)ester, cyano, phosphoryl, amino, imino, (thio)amido, sulfhydryl, alkylthio, acylthio, sulfonyl, a sulfate, a sulfonate, a sulfamoyl, a sulfonamido, nitro, azido, haloalkyl, including perfluoroalkyl (such as trifluoromethyl), haloalkoxy, alkylsulfanyl, alkylsulfinyl, alkylsulfonyl, alkylsulfonylamino, arylsulfonoamino, phosphoryl, phosphate, phosphonate, phosphinate, alkylcarboxy, alkylcarboxyamide, oxo, hydroxy, mercapto, amino (optionally mono- or di-substituted, e.g. by alkyl, aryl, or heteroaryl), imino, carboxamide, carbamoyl (optionally mono- or di-substituted, e.g. by alkyl, aryl, or heteroaryl), amidino, aminosulfonyl, acylamino, aroylamino, (thio)ureido, (arylthio)ureido, alkyl(thio)ureido, cycloalkyl(thio)ureido, aryloxy, aralkoxy, or —O(CH$_2$)$_n$—OH, —O(CH$_2$)$_n$—NH$_2$, —O(CH$_2$)$_n$COOH, —(CH$_2$)$_n$COOH, —C(O)O(CH$_2$)$_n$R, —(CH$_2$)$_n$N(H)C(O)OR, or —N(R)S(O)$_2$R wherein n is 1-4 and R is independently selected from hydrogen, -alkyl, -alkenyl, -alkynyl, -cycloalkyl, -cycloalkenyl, —(C-linked-heterocycloalkyl), —(C-linked-heterocycloalkenyl), -aryl, and -heteroaryl, with multiple degrees of substitution being allowed. It will be understood by those skilled in the art that substituents, such as heterocycloalkyl, aryl, heteroaryl, alkyl, etc., or functional groups such as —OH, —NHR etc., can themselves be substituted, if appropriate. It will also be understood by those skilled in the art that the substituted moieties themselves can be substituted as well when appropriate.

In particular embodiments, the linker L comprises a moiety selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—).

In particular embodiments of the present invention, the linker L comprises a number of m groups selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted, the linker further comprises a number of n moieties independently selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—), wherein m=n+1. In particular embodiments, m is 2 and n is 1, or m is 3 and n is 2. In particular embodiments, the linker comprises 2 or 3 unsubstituted alkylene groups, and 1 or 2, respectively, disulfide, ether, thioether, amine, ester, carboxamide, urethane or urea moieties linking the unsubstituted alkylene groups.

In particular embodiments, the C atoms in the linear chain are independently part of optionally substituted methylene groups (—CH$_2$—). In particular such embodiments, the optional substituents are independently selected from halogen and C$_{1-6}$-alkyl, particularly methyl.

In particular embodiments, the linker L is a stable linker.

In the context of the present invention, the term "stable linker" refers to a linker that is stable (i) in the presence of enzymes, and (ii) in an intracellular reducing environment.

In particular embodiments, the stable linker does not contain (i) an enzyme-cleavable substructure, and/or (ii) a disulfide group. In particular such embodiments, the linker has a length of up to 12 atoms, particularly from 2 to 10, more particularly from 4 to 9, and most particularly from 6 to 8 atoms.

In particular other embodiments, the linker is a cleavable linker.

In the context of the present invention, the term "cleavable linker" refers to a linker that is (i) cleavable by an enzyme, or (ii) a reducible linker.

In the context of the present invention, the term "reducible linker" refers to a linker that can be cleaved in the intracellular reducing environment, particularly a linker that contains a disulfide groups, resulting in the intracellular release of the toxin cargo conjugated to the targeting antibody after internalization by the intracellular reducing environment (see Shen et al., J. Biol. Chem. 260 (1985) 10905-10908). In particular embodiments, the reducible linker comprises a moiety

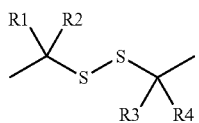

wherein R1 to R4 are independently selected from H and methyl.

In particular other embodiments, the linker is a cleavable linker, particularly (i) a linker cleavable by an enzyme, or (ii) a reducible linker, particularly a linker comprising a disulfide group. In particular such embodiments, such cleavable linker has a length of up to 20 atoms, particularly from 6 to 18, more particularly from 8 to 16, and most particularly from 10 to 15 atoms.

In particular embodiments, the cleavable linker comprises a structure $L^1$-$L^*$-$L^2$

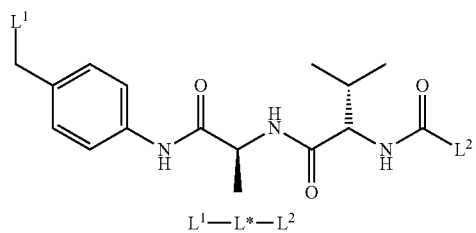

$L^1$—$L^*$—$L^2$ wherein $L^1$ is a part of the linker that connects $L^*$ to the amatoxin, in particular, wherein $L^1$ is connected to $L^*$ via a —NH— or a —O— group, particularly a —C(=O)—NH—, a —C(=O)—NH—O— or a —C(=O)—O— group, and wherein $L^2$ is a part of the linker that connects $L^*$ to the target-binding moiety, in particularly wherein $L^1$ is connected to $L^*$ via a —(CH$_2$)$_m$— moiety, with m being an integer selected from 1 to 8, in particular from 1 to 5, or via a —(CH$_2$CH$_2$O)$_n$— moiety, with n being an integer selected from 1 to 3, in particular from 1 to 2.

In particular other embodiments, $L^*$ has the following structure

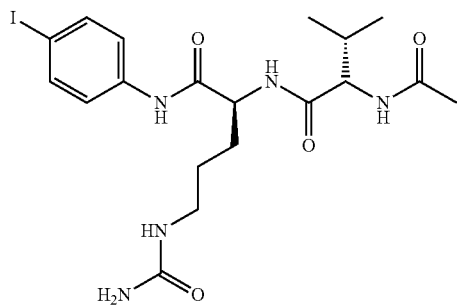

In particular embodiments, said linker is present and is connected on one side to a position in γ-amaninamide (1; x=0, 1 or 2), γ-amaninamidic acid (2; x=0, 1 or 2), or γ-amaninamidic hydroxamic acid (3; x=0, 1 or 2) selected from (i) in the case of compound 1, the nitrogen atom of the amide group at the γ C-atom of amatoxin amino acid 1 (amide linkage);

(ii) in the case of compound 2, the oxygen atom of the acid group at the γ C-atom of amatoxin amino acid 1 (ester linkage);

(iii) in the case of compound 3, the oxygen atom of the hydroxamic acid group at the γ C-atom of amatoxin amino acid 1;

(iv) the oxygen atom of the hydroxy group at the δ C-atom of amatoxin amino acid 3, particularly via an ester linkage, an ether linkage or a urethane linkage; or (v) the 6' C-atom of amatoxin amino acid 4; and (vi) the ring nitrogen of amino acid 4.

In particular embodiments, said linker is present and is connected on the other side to the target-binding moiety via a urea moiety ( . . . -linker-NH—C(=O)—H— target-binding moiety). In particular such embodiments, the urea moiety results from a reaction of a primary amine originally present in the target-binding moiety, such as an amino group of a lysine side chain, with a carbamic acid derivative . . . -linker-NH—C(O)—Z, wherein Z is a leaving group that can be replaced by a primary amine.

In particular other embodiments, said linker is present and is connected on the other side to the target-binding moiety via a thioether moiety ( . . . -linker-S-target-binding moiety). In particular such embodiments, the thioether moiety results from a reaction of a thiol group originally present in the target-binding moiety, such as a thiol group of a cysteine side chain, with a thiol-reactive group.

In the context of the present invention, the term "thiol-reactive group" refers to a group that selectively reacts with the thiol group of a free cysteine of an antibody, particularly in a pH value in the range between 6.0 and 8.0, more particularly in a pH value in the range between 6.5 and 7.5. In particular, the term "selectively" means that less than 10% of the coupling reactions of a molecule comprising a thiol-reactive group with an antibody comprising at least one free cysteine residue are coupling reactions with non-cysteine residues of the antibody, such as lysine residues, particularly less than 5%, more particularly less than 2%.

In particular embodiments, the moiety resulting from coupling of a thiol group to a thiol-reactive group is selected from: thiol-substituted acetamide; thiol-substituted succinimide; thiol-substituted succinamic acid; thiol-substituded heteroaryl, particularly thiol-substituted benzothiazole, thiol-substituted phenyltetrazole and thiol-substituted phenyloxadiazole; and a disulphide, wherein one sulphur atom is derived from a cysteine residue of the antibody. In particular embodiments, the moiety resulting from coupling of a thiol group to a thiol-reactive group is a thiol-substituted succinimide.

In a seventh aspect, the present invention relates to conjugates of γ-amaninamide (1; x=0, 1 or 2), γ-amaninamidic acid (2; x=0, 1 or 2), or γ-amaninamidic hydroxamic acid (3; x=0, 1 or 2) with a linking moiety, which is connected on one side to a position or functional group present in said γ-amaninamide (1; x=0, 1 or 2), γ-amaninamidic acid (2; x=0, 1 or 2), or γ-amaninamidic hydroxamic acid (3; x=0, 1 or 2) and which further comprises a position or functional group, which can directly or indirectly be connected to a position or functional group present in a target-binding moiety, particularly wherein said target-binding moiety is an antibody or a fragment of an antibody comprising at least a functional antigen-binding domain.

In a particular embodiment, x is selected from 1 and 2, and in particular is 1.

In particular embodiments, said position or functional group, which can directly or indirectly be connected to a position or functional group present in a target-binding moiety is a carbamic acid derivative —NH—C(O)—Z, wherein Z is a leaving group that can be replaced by a nucleophilic group of a target-binding moiety, particularly by a primary amine of a target-binding moiety.

In particular embodiments, said position or functional group, which is on one side connected to the linker and which can directly or indirectly be connected to a position or functional group present in a target-binding moiety, is a thiol-reactive group. In particular embodiments, the thiol-reactive group is selected from iodoacetamide, maleimide, a maleimide having a leaving group in position 3, in particular a leaving group selected from —Br, and substituted thiol (see, for example, U.S. Pat. No. 9,295,729), a 1,2-dihydropyridazine-3,6-dione having a leaving group in position 4, in particular a leaving group selected from —Br, and substituted thiol (see, for example, U.S. Pat. No. 9,295,729), methylsulfonyl benzothiazole, methylsulfonyl phenyltetrazole, methylsulfonyl phenyloxadiazole (see Toda et al., Angew. Chem. Int. Ed. Engl., 52 (2013) 12592-6), and 5-nitro-pyridin-2-yl-disulfide ( . . . -L-S—S-(5-nitro-pyridine-2-yl).

In particular embodiments, said position or functional group, which is on one side connected to the linker and which can directly or indirectly be connected to a position or functional group present in a target-binding moiety is a moiety that can react with two thiol groups present in one target-binding moiety or in two target-binding moieties. In particular embodiments, the thiol-reactive groups is a maleimide having two leaving groups in positions 3 and 4, in particular selected from 3,4-dibromomaleimide, 3,4-bis(arylthio)-maleimide, in particular 3,4-diphenylthio-maleimide, and 3,4-bis(heteroarylthio)-maleimide, in particular 3,4-bis(2-pyridinyl-sulfanyl)-maleimide, and. In particular other embodiments, the thiol-reactive groups is a 1,2-dihydropyridazine-3,6-dione having two leaving groups in positions 4 and 5, in particular selected from 4,5-bromo-1,2-dihydropyridazine-3,6-dione, 4,5-bis(arylthio)-1,2-dihydropyridazine-3,6-dione, in particular 4,5-diphenylthio-1,2-dihydropyridazine-3,6-dione, and 4,5-bis(heteroarylthio)-1,2-dihydropyridazine-3,6-dione, in particular 4,5-bis(2-pyridinyl-sulfanyl)-1,2-dihydropyridazine-3,6-dione.

In particular embodiments, the position or functional group, which can directly or indirectly be connected to a position or functional group present in a target-binding moiety, is not an ethynyl group, or, more generally, is not an alkynyl group, or is not a group that can be reacted with an 1,3 dipole in a 1,3-dipolar cycloaddition (click chemistry).

In another aspect the present invention relates to an amatoxin of the present invention, particularly selected from γ-amaninamide (1; x=0, 1 or 2), γ-amaninamidic acid (2; x=0, 1 or 2), and γ-amaninamidic hydroxamic acid (3; x=0, 1 or 2), or to a conjugate of the present invention of an amatoxin with a target-binding moiety, for use as a medicament.

In another aspect the present invention relates to an amatoxin of the present invention, particularly selected from γ-amaninamide (1; x=0, 1 or 2), γ-amaninamidic acid (2; x=0, 1 or 2), and γ-amaninamidic hydroxamic acid (3; x=0, 1 or 2), or to a conjugate of the present invention of an amatoxin with a target-binding moiety, for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, leukemia, and malignant lymphoma.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein "administering" includes in vivo administration, as well as administration directly to tissue ex vivo, such as vein grafts.

In particular embodiments, a therapeutically effective amount of the conjugate of the present invention is used.

A "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In another aspect the present invention relates to pharmaceutical composition comprising an amatoxin according to the present invention, or a conjugate of the present invention of an amatoxin with a target-binding moiety, and further comprising one or more pharmaceutically acceptable diluents, carriers, excipients, fillers, binders, lubricants, glidants, disintegrants, adsorbents; and/or preservatives.

"Pharmaceutically acceptable" means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxin conjugates of the invention to proteins or polymers or they can also be added with the aim to reduce the adsorption of the target-binding moiety toxin conjugates of the invention to materials like injection instruments or packaging-materials, for example, plastic or glass.

The amatoxins of the present invention comprising a target-binding moiety can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the target-binding moiety toxin conjugates of the invention are introduced in finely dispersed, dispersed and suspended form, respectively, or as a suspension of crystals in the medicament or based on the "single unit principle" if the target-binding moiety toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are preferably aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the target-binding moiety toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The target-binding moiety toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

EXAMPLES

In the following, the invention is explained in more detail by non-limiting examples:

1. Synthesis of benzyl (2S,3R,4S)-2-((((9H-fluoren-yl)methoxy)carbonyl)amino)-4-acetoxy-3-methyl-pentanoate HDP 30.1485

HDP 30.1485

1.1 Synthesis of (2S,3R,4S)-4-acetoxy-3-methyl-pentanoic acid complex HDP 30.1409

HDP 30.1409

Step 1.1.1:

Under argon 4.47 g (18.3 mmol) 9-borabicyclo[3.3.1]nonane (9-BBN) dimer were added to 120 ml dry methanol. The mixture was heated at reflux for 30 min until the 9-BBN was completely dissolved. The clear solution was cooled to 50° C. and 4.86 g (33.0 mmol) (2S,3R,4S)-2-amino-4-hydroxy-3-methyl-pentanoic acid were added. The resultant suspension was heated for an additional time of 3 h, during which time gas evolution ceased and the suspension became a clear homogeneous solution. The methanolic solution was chilled in an ice bath and the crystalline product was filtered off yielding 5.65 g of chromatographically pure (silica gel; n-hexane/ethyl acetate/methanol (10/10/1), ninhydrin) amino acid-boron complex. The filtrate was evaporated to dryness and the remaining residue purified on silica gel with a gradient of n-hexane to n-hexane/ethyl acetate/methanol (10/10/1) yielding an additional amount of 1.73 g of the amino acid-boron complex. The total yield was 7.38 g (84% yield).

MS (ES+) found: 268.09 [MH]+; calc.: 267.20 (C14H26BNO3)

Step 1.1.2:

The complex was dissolved in a mixture of 360 ml dry THF and pyridine (7.38 ml (91.3 mmol). 1.85 ml (25.9 mmol) acetyl chloride were added at room temperature. After 4 h stirring pyridine (7.38 ml (91.3 mmol)) and acetyl chloride (1.85 ml (25.9 mmol)) were added. Stirring was continued for 4 h, and the reaction mixture was filtered and evaporated to dryness. The residue was purified by flash chromatography on silica gel with a gradient of n-hexane to ethyl acetate yielding 4.34 g (59%) of a white crystalline mass of the O-acetyl boron complex HDP 30.1409.

MS (ESI+) found: 310.07 [MH]+; calc.: 309.21 (C16H28BNO4)

MS (ESI+) found: 332.13 [M+Na]+; calc.: 332.21 (C16H28BNNaO4)

$^1$H NMR (500 MHz, methanol-d4) δ 5.08 (dq, J=9.6, 6.2 Hz, 1H), 3.85 (d, J=2.8 Hz, 1H), 2.30 (dqd, J=9.8, 7.0, 2.7 Hz, 1H), 2.02 (s, 3H), 1.95-1.70 (m, 8H), 1.65 (dt, J=19.0, 7.4 Hz, 2H), 1.49-1.40 (m, 2H), 1.27 (d, J=6.2 Hz, 3H), 1.07 (d, J=7.1 Hz, 3H), 0.53 (s, 2H).

$^{13}$C NMR (126 MHz, methanol-d4) δ 175.83, 172.02, 72.88, 57.55, 49.51, 40.79, 32.76, 32.55, 32.25, 31.93, 25.52, 25.22, 21.15, 18.61, 13.02.

1.2 Synthesis of (2S,3R,4S)-2-((((9H-fluoren-yl)methoxy)carbonyl)amino)-4-acetoxy-3-methylpentanoate HDP 30.1427

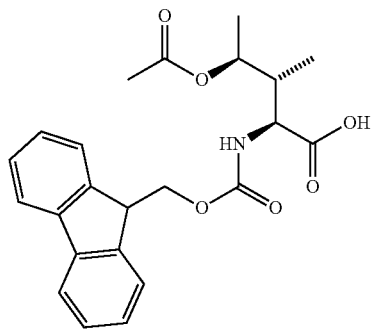

HDP 30.1427

4.14 g (13.4 mmol) of HDP 30.1409 were suspended in 35 ml methanol. 210 ml chloroform were added and the clear solution was stirred for 24 h at 23° C. Chloroform and methanol were evaporated in vacuum and the residue was redissolved in a freshly prepared methanol/chloroform (35 ml/210 ml) mixture. The solution was heated to 50° C. for 6 h and evaporated to dryness. The remaining residue was treated with 700 ml diethyl ether and stirred for 60 minutes. The resulting suspension was filtered off, and the white solid dried in vacuum. The solid was resuspended in 90 ml 1,4-dioxane and 65 ml acetone. 60 ml of a 0.8 M aqueous NaHCO3-solution were added. The two phase mixture was treated at once with 5.24 g (15.5 mmol) N-(fluorenyl-9-methoxycarbonyloxy)-succinimide (FmocOSu).

The mixture was stirred under argon at room temperature for 17 h and acidified with 5% citric acid. The aqueous phase was extracted 3 times with diethyl ether. The combined ether phases were washed 3 times with water and dried over sodium sulphate. The crude acid was purified by silica gel chromatography with a gradient of CHCl3 containing 1% acetic acid to a mixture of CHCl3/MeOH (40/1) containing 1% acetic acid. Evaporation of the product fractions gave 2.48 g (45% yield) HDP 30.1427 as a white crystalline mass.

MS (ESI+) found: 412,23[MH]+; calc.: 411.17 (C23H25N6)

$^1$H NMR (500 MHz, chloroform-d) δ 7.77 (d, J=7.6 Hz, 2H), 7.61 (t, J=6.7 Hz, 2H), 7.44-7.37 (m, 2H), 7.32 (tdd, J=7.5, 2.8, 1.2 Hz, 2H), 5.54 (d, J=9.3 Hz, 1H), 4.93-4.84 (m, 1H), 4.50 (dd, J=9.2, 3.1 Hz, 1H), 4.44-4.33 (m, 2H), 4.25 (t, J=7.4 Hz, 1H), 2.51-2.41 (m, 1H), 2.04 (s, 3H), 1.26 (d, J=6.0, Hz 3H), 1.04 (d, J=7.0 Hz, 3H).

$^{13}$C NMR (126 MHz, CDCl3) δ 176.26, 171.23, 156.48, 143.77, 143.59, 141.24, 127.70, 127.06, 125.12, 71.22, 67.36, 55.93, 47.04, 41.21, 21.11, 18.43, 14.27.

1.3 Synthesis of compound 6 (benzyl (2S,3R,4S)-2-((((9H-fluoren-yl)methoxy)carbonyl)-amino)-4-acetoxy-3-methylpentanoate (HDP 30.1485)

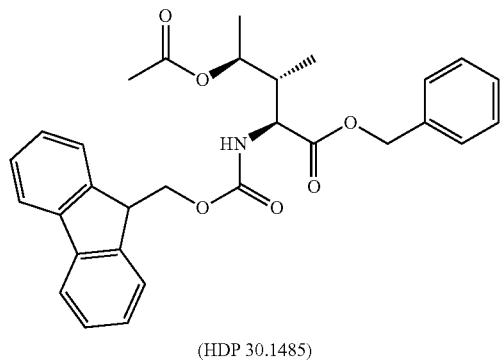 [SMILES: CC(=O)O[C@@H](C)[C@H](C)[C@H](NC(=O)OCC1c2ccccc2-c2ccccc21)C(=O)OCc1ccccc1]

Compound 6

(HDP 30.1485)

A solution of 2.47 g (6.00 mmol) HDP 30.1427 in 120 ml dry methanol was treated over an hour with 225 ml of a 0.03 M phenyldiazomethane solution in toluene. The phenyldiazomethane solution was prepared according to Zhou et al., J. Am. Chem. Soc., 131 (2009) 11734-11743. After the N2 liberation has ceased, the reaction mixture was stirred under argon for an additional hour. The progress of the reaction was monitored by TLC (SiO2, n-hexane/ethyl acetate (1/1)) and evaporated to dryness after completion. The residue was purified by silicagel chromatography with a gradient of n-hexane to ethylacetate. Pure fractions were combined and evaporated to a white solid of HDP 30.1485.

Yield: 2.41 g (80%)

MS (ESI+) found: 524.43 [M+Na]+; calc.: 524.22 (C30H31NaNO6)

$^1$H NMR (500 MHz, chloroform-d) δ 7.76 (d, J=7.5 Hz, 2H), 7.61 (t, J=7.3 Hz, 2H), 7.44-7.27 (m, 9H), 5.53 (d, J=9.3 Hz, 1H), 5.18 (s, 2H), 4.92-4.82 (m, 1H), 4.50 (dd, J=9.3, 3.4 Hz, 1H), 4.37 (qd, J=10.6, 7.4 Hz, 2H), 4.24 (t, J=7.4 Hz, 1H), 2.44 (ddt, J=13.5, 10.0, 5.0 Hz, 1H), 1.98 (s, 3H), 1.23 (d, J=6.2 Hz, 3H), 0.99 (d, J=7.0 Hz, 3H).

$^{13}$C NMR (126 MHz, CDCl3) δ 171.56, 170.84, 156.49, 143.88, 143.66, 141.22, 135.18, 128.64, 128.24, 127.65, 127.05, 125.16, 119.91, 76.71, 70.99, 67.30, 67.14, 56.18, 47.08, 41.19, 21.05, 18.28, 14.22.

2. Synthesis of HDP 30.0287

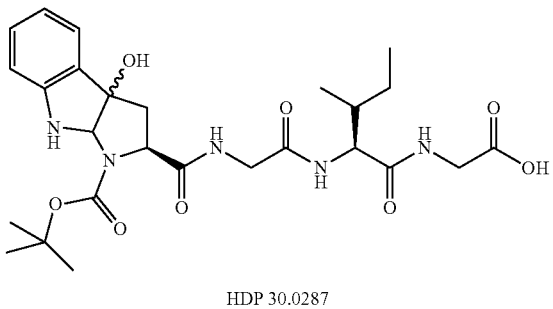 [SMILES: CCC(C)[C@H](NC(=O)CNC(=O)[C@@H]1CC2(O)c3ccccc3NC2N1C(=O)OC(C)(C)C)C(=O)NCC(=O)O]

HDP 30.0287

2.1 Synthesis of HDP 30.0081 (TrNH-Gly-Ile-OMe)

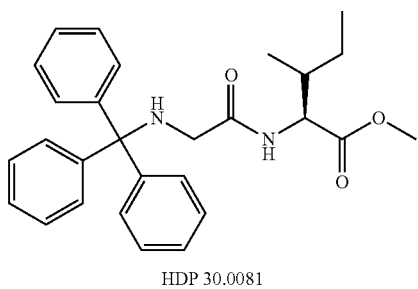 [SMILES: CCC(C)[C@H](NC(=O)CNC(c1ccccc1)(c1ccccc1)c1ccccc1)C(=O)OC]

HDP 30.0081

1.59 g (5.00 mmol) N-tritylglycine and 0.91 g (5.00 mmol) L-isoleucine-methylester hydrochloride were suspended in 25 ml dry dichloromethane and treated with 0.87 ml (5.00 mmol) N-ethyl-diisopropylamine (DIPEA). 0.77 g (5.00 mmol) N-hydroxybenzotriazole hydrate (HOBt×H$_2$O) were added to the clear solution. The reaction mixture was flushed with argon. Then 5.00 ml of a 1 M solution of dicyclohexylcarbodiimide (DCC) in dichloromethane were added at room temperature. The clear solution became turbid after few minutes. The reaction mixture was stirred under argon at room temperature for 20 h. The crystalline insoluble dicyclohexylurea was filtered off and washed with dichloromethane. The dichloromethane-phase was evaporated on a rotatory evaporator and the semisolid residue was taken up in 25 ml ethyl acetate. Insoluble additional dicyclohexylurea was filtered off and the ethylacetate solution was evaporated obtaining a yellow oil, which was purified on a silicagel column with a gradient from CHCl$_3$ to CHCl$_3$/MeOH (40/1). Evaporation of the fractions in vacuum gave 2.07 g (93%) HDP 30.0081 as a white foam.

MS (ESI$^+$) found: 445.43 [MH]$^+$; calc.: 444.24 (C$_{28}$H$_{32}$N$_2$O$_3$)

2.2 Synthesis of HDP 30.0083 (TrNH-Gly-Ile-OH)

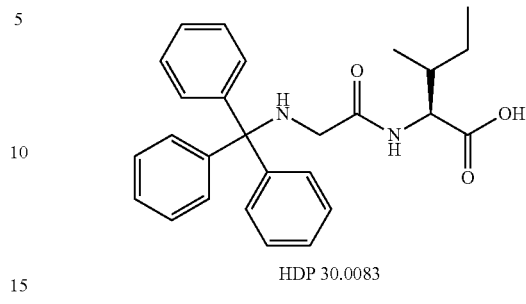

HDP 30.0083

The solution of 5.40 g (12.15 mmol) TrNH-Gly-Ile-OMe in 50 ml methanol was treated with 26 ml of a 2 M solution of LiOH in water. The resulting suspension was stirred for 20 hours at ambient temperature under argon. Finally the clear solution was evaporated to dryness. The remaining residue was distributed between a mixture of 100 ml CHCl$_3$ and 100 ml 5% aqueous citric acid. The CHCl$_3$ phase was washed with water and brine and dried over MgSO$_4$. After evaporation of the solvent pure HDP 30.0083 was obtained as a colourless oil which solidified in vacuum to a white foam (3.50 g, 67%).

MS (ESI$^+$) found: 431,48[MH]$^+$; calc.: 430.23 (C$_{27}$H$_{30}$N$_2$O$_3$)

2.3 Synthesis of HDP 30.0084 (TrNH-Gly-Ile-Gly-OMe)

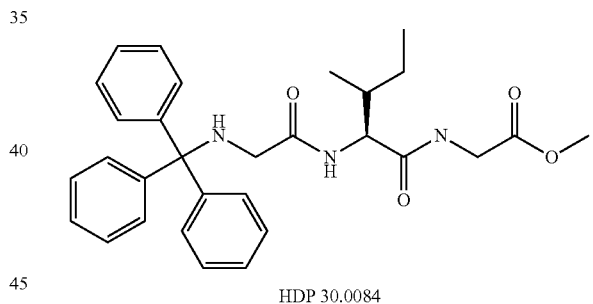

HDP 30.0084

7.20 g (16.70 mmol) HDP 30.0083 TrNH-Gly-Ile-OH and 2.10 g (16.70 mmol) glycine methylester hydrochloride were suspended in 125 ml dry dichloromethane. After addition of 2.85 ml (16.70 mmol) N-ethyl-diisopropylamine (DIPEA), 2.57 g (16.70 mmol) N-hydroxybenzotriazole hydrate (HOBt×H$_2$O) was added and the reaction mixture was flushed with argon. 3.46 g (16.70 mmol) dicyclohexylcarbodiimide (DCC) were added at room temperature and the reaction mixture was stirred under argon at room temperature for 24 h. The insoluble dicyclohexyl urea was filtered off and washed with dichloromethane. The dichloromethane phase was evaporated on a rotatory evaporator and the crude residue (12.43 g) was taken up in 30 ml chloroform. Insoluble dicyclohexyl urea was filtered off, and the chloroform solution was purified on a silicagel column with a gradient from CHCl$_3$ to CHCl$_3$/MeOH (40/1). Evaporation of the product fractions in vacuum gave 3.55 g (42%) of a white solid.

MS (ESI$^+$) found: 501.29 [MH]$^+$; calc.: 501.26 (C$_{30}$H$_{35}$N$_3$O$_4$)

MS (ESI⁺) found: 524.33 [M+Na]⁺; calc.: 524.26 ($C_{30}H_{35}N_3NaO_4$)

2.4 Synthesis of HDP 30.0089 (H₂N-Gly-Ile-Gly-OMe)

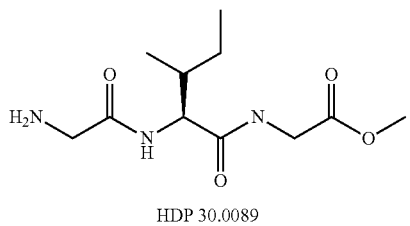 [SMILES: CCC(C)[C@H](NC(=O)CN)C(=O)NCC(=O)OC]

HDP 30.0089

2.03 g (4.05 mmol) HDP 30.0084 TrNH-Gly-Ile-Gly-OMe were dissolved in 110 ml dry dichloromethane. Trifluoroacetic acid (1.50 ml) was added and the yellow solution stirred for 4 h under argon at room temperature. The gelling reaction mixture was treated with 50 ml methanol und stirred for an additional hour. The colourless and clear solution was evaporated to dryness und the remaining residue was stirred with 100 ml diethyl ether overnight. The white solid was filtered off and dried in vacuum.

1.40 g (71%) white solid of H₂N-Gly-Ile-Gly-OMe×TFA
MS (ESI⁺) found: 260.23[MH]⁺; calc.: 259.15 ($C_{11}H_{21}N_3O_4$)

2.5 Synthesis of HDP 30.0263 (BocHpi-Gly-Ile-Gly-OMe)

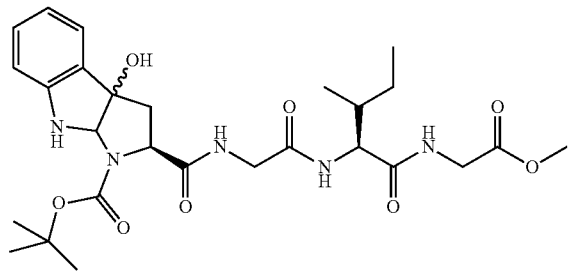

HDP 30.0263

To a solution of 2.27 g (5.33 mmol) BocHpi (1-Boc-L-3a-hydroxy-1,2,3,3a,8,8a-hexahydropyrrolo[2,3-b]-indole-2-carboxylic acid (Droste, H., Wieland, T., Liebigs Annalen der Chemie 11 (1987) 901-10; and Savige, W. E., Aust. J. Chem. 1975, 2275-2287) in 50 ml dry dimethylformamide, 1.96 g (5.26 mmol) H₂N-Gly-Ile-Gly-OMe (HDP 30.0089), 1.83 ml (10.49 mmol) N-ethyl-diisopropylamine (DIPEA) and 2.74 g (5.27 mmol) PyBOP (benzotriazol-1-yl-oxytripyrrolidinophosphonium hexafluorophosphate) were added at ambient temperature. The reaction mixture was stirred for 14 h at room temperature under argon atmosphere and diluted with 150 ml chloroform. The organic solution was extracted with 5% citric acid (1×), saturated NaHCO₃-solution (1×) and water (3×), dried over MgSO₄, filtered off and evaporated to dryness. The solid residue was purified on a silica-gel-column with a gradient from CHCl₃ to CHCl₃/MeOH (10/1) as eluent. HDP 30.0263 was obtained as a white solid.

Yield: 1.79 g (60%).
MS (ESI⁺) found: 562.34 [MH]⁺; calc.: 561.28 ($C_{27}H_{39}N_5O_8$)
MS (ESI⁺) found: 584.41 [M+Na]⁺; calc.: 584.28 ($C_{27}H_{39}N_5NaO_8$)

2.6 Synthesis of HDP 30.0287 (BocHpi-Gly-Ile-Gly-OH)

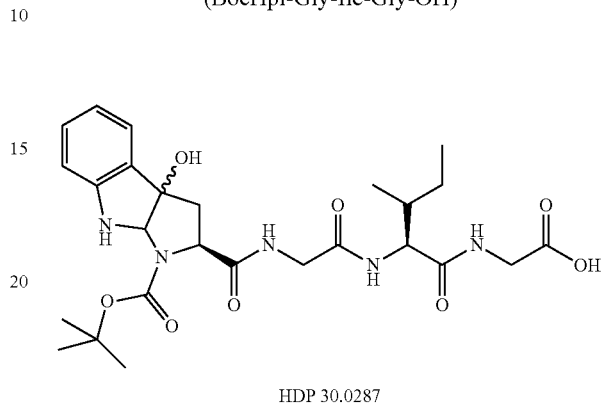

HDP 30.0287

A solution of 280.5 mg (0.50 mmol) BocHpi-Gly-Ile-Gly-OMe (HDP 30.0263) in 7.5 ml dry methanol was treated with 550 µl of a 2 M solution of LiOH in water. The reaction mixture was stirred for 3 h at ambient temperature under argon. After completion, the reaction was quenched with 500 µl acetic acid (TLC (SiO₂): CHCl₃/MeOH/1% AcOH) and evaporated to dryness. The residue was purified on silica gel with a gradient of CHCl₃ containing 1% AcOH to CHCl₃/MeOH (9/1) containing 1% AcOH. Yield: 225 mg (82%).

S (ESI⁺) found: 548.10 [MH]⁺; calc.: 547.26 ($C_{26}H_{37}N_5O_6$)
MS (ESI⁺) found: 570.30 [M+Na]⁺; calc.: 570.26 ($C_{26}H_{37}N_5NaO_6$)
MS (ESI+) found: 1095.10 [2M+H]⁺

3. Synthesis of Gamma-Amaninamid HDP 30.1790

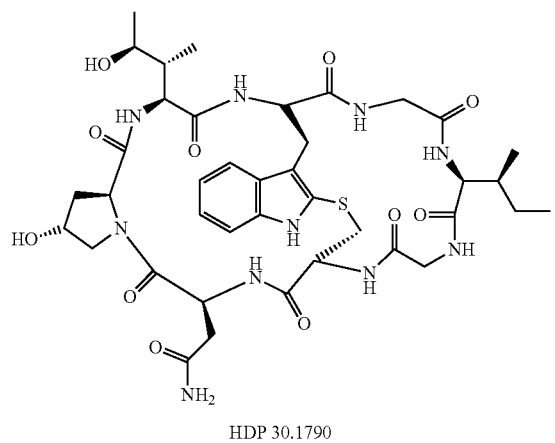

HDP 30.1790

3.1 Synthesis of HDP 30.1788

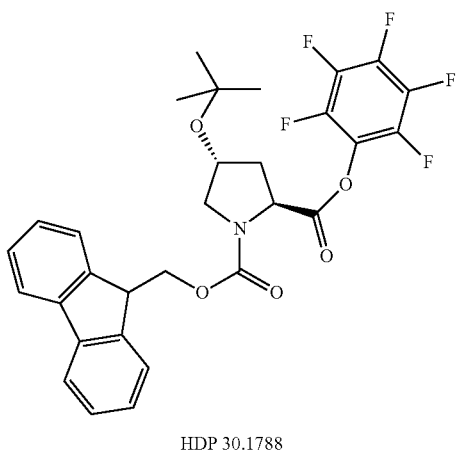 [SMILES: CC(C)(C)O[C@@H]1C[C@@H](C(=O)Oc2c(F)c(F)c(F)c(F)c2F)N(C(=O)OCC2c3ccccc3-c3ccccc32)C1]

HDP 30.1788

2000 mg (4.88 mmol) FmocN-Hyp(O'Bu)OH were dissolved in 35 ml dry ethyl acetate and treated with 904 mg (4.91 mmol) pentafluorophenol, dissolved in 5 ml ethyl acetate, and 1112 mg (5.39 mmol) dicyclohexylcarbodiimide (DCC), dissolved in 5 ml ethyl acetate. After 20 h stirring at room temperature under argon, the precipitated urea was filtered off and washed with etylacetate. The organic solvent was evaporated and the remaining highly viscous colourless oil was dried in high vacuum. Yield: 2.45 g (87%). The sufficiently pure product was used for the next step without further purification.

MS (ESI$^+$) found: 576.23 [MH]$^+$; calc.: 575.17 ($C_{30}H_{26}F_5NO_5$)

3.2 Synthesis of HDP 30.1502

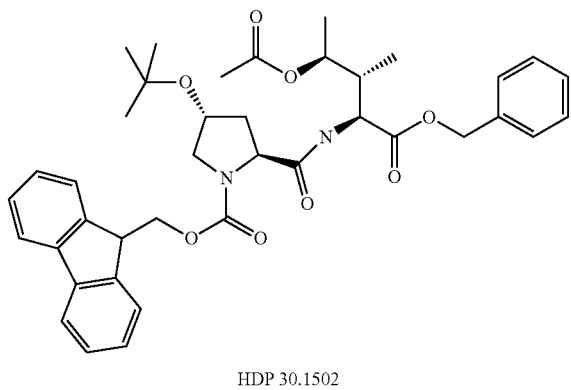 [SMILES: CC(=O)O[C@@H](C)[C@H](C)[C@H](NC(=O)[C@@H]1C[C@@H](OC(C)(C)C)CN1C(=O)OCC1c2ccccc2-c2ccccc21)C(=O)OCc1ccccc1]

HDP 30.1502

Route A:

815.0 mg (1.63 mmol) HDP 30.1485 were dissolved in 35 ml dry dimethylformamide. After addition of 473 µl (4.55 mmol) diethylamine, the reaction mixture was stirred at room temperature under argon for 2.5 h. Excess diethylamine was removed in vacuum with a rotatory evaporator at 35° C. and 40 mm Hg (left for 1 h in vacuum). Then the dimethylformamide solution was treated with 1870.0 mg (3.25 mmol) HDP 30.1788 FmocN-Pro(OtBu)-O5FPh and 283.0 µl (1.63 mmol) N-ethyl-diisopropylamine (DIPEA). The reaction mixture was stirred under argon. After 19 h the solution was diluted with chloroform and washed with 5% citric acid (1×) and with water (3×). After drying over sodium sulphate the volatiles were evaporated and the residue purified on silica gel with linear gradient of n-hexane to ethylacetate. The product fractions were collected and the solvents evaporated to a white solid. Yield: 83.0 mg (8%).
Route B (Ueki et al., Chem. Lett. 1993, 721-724):

To 2.41 g (4.80 mmol) HDP 30.1485 dissolved in 24 ml dry dimethylformamide, 8.31 ml (47.87 mmol, 10.0 equivalents) 1-octanethiol and 3.03 g (11.59 mmol, 2.4 equivalents) tetrabutylammonium fluoride hydrate were added. After sonification for one minute 6.6 g (28.8 mmol) bis-(1-methyl-1H-tetrazole-5yl) disulfide were added at once. The yellow solution was sonificated for 3 min and treated with 3.01 ml (17.28 mmol) N-ethyldiisopropylamine (DIPEA) and 3.21 g (5.59 mmol) HDP 30.1788 dissolved in 24 ml dry dimethylformamide. After 30 min of stirring under argon at ambient temperature the reaction mixture was diluted with 50 ml 5% aqueous NaHCO$_3$ solution. The mixture was extracted with ethyl acetate, and the organic phase was washed 3 times with water. After drying over sodium sulphate, the organic solvent was evaporated and the remaining yellow oil dried in high vacuum. Yield: 12.1 g. The crude material was purified on silica gel with a linear gradient of n-hexane to ethylacetate. The product fractions were collected and the solvent evaporated to a white solid. Yield 1.50 g (49%).

MS (ESI$^+$) found: 671.31 [MH]$^+$; calc.: 670.33 ($C_{39}H_{46}N_2O_8$)

MS (ESI$^+$) found: 693.50 [M+Na]$^+$; calc.: 693.33 ($C_{39}H_{46}N_2NaO_8$)

3.3 Synthesis of HDP 30.1170
(FmocNH-Cys(STr)-Asn(NHTr)-OH)

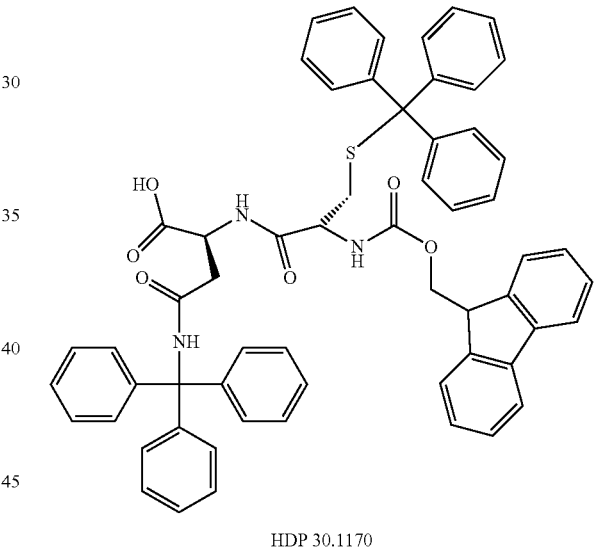

HDP 30.1170

To a solution of 2085 mg (5.57 mmol) H$_2$N-Asn(NHTr) OH in 75 ml dry dimethylformamide, 3798 mg (5.56 mmol) FmocNH-Cys(STr)ONHS and 3000 µl N,N-ethyl-diisopropylamine (DIPEA) were added. The reaction mixture was stirred at room temperature under argon. After 22 h the mixture was diluted with chloroform and extracted with 5% aqueous citric acid (1×) and water (3×). The organic solvent was dried over MgSO$_4$ and evaporated. The solid residue was purified by column chromatography on silica gel using a gradient of CHCl$_3$ containing 1% AcOH to CHCl$_3$/MeOH (40/1) containing AcOH as eluent. Pure fractions of the product were collected and evaporated to dryness yielding 3010 mg (53%) white crystals.

MS (ESI$^+$) [M+Na]$^+$ found: 964.21; calc.: 964.34 ($C_{60}H_{51}N_3NaO_6S$)

MS (ESI$^+$) [2M+H]$^+$ found: 1882.43; calc.: 1883.71 ($C_{120}H_{103}N_6O_{12}S_2$)

MS (ESI$^+$)[2M+Na]$^+$ found: 1904.79; calc.: 1905.69 ($C_{120}H_{102}N_6NaO_{12}S_2$)

3.4 Synthesis of HDP 30.1668

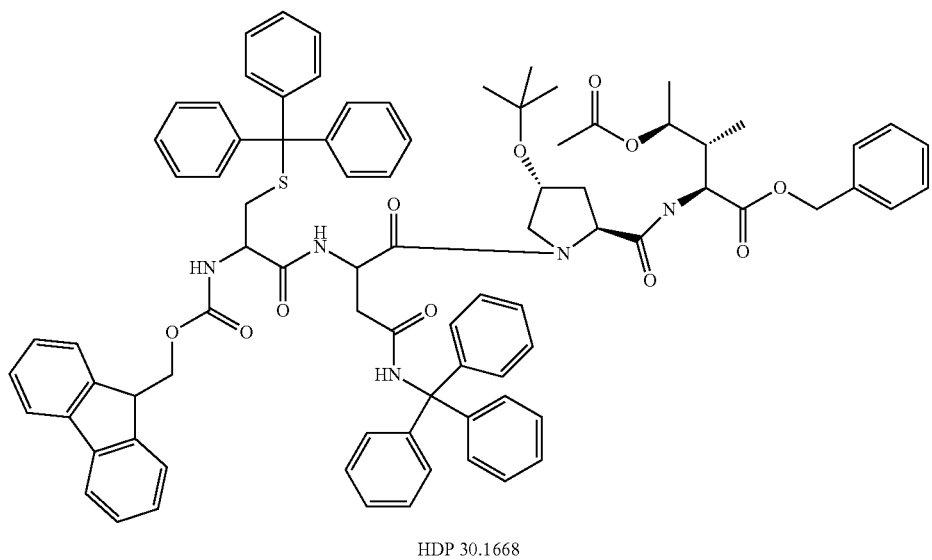 [SMILES: CC(=O)O[C@@H](C)[C@H](C)[C@H](NC(=O)[C@@H]1C[C@@H](OC(C)(C)C)CN1C(=O)C(CC(=O)NC(c1ccccc1)(c1ccccc1)c1ccccc1)NC(=O)C(CSC(c1ccccc1)(c1ccccc1)c1ccccc1)NC(=O)OCC1c2ccccc2-c2ccccc21)C(=O)OCc1ccccc1]

HDP 30.1668

213.0 mg (0.32 mmol) HDP 30.1502 were dissolved in 11 ml dry dimethylformamide. After addition of 93.0 µl (0.89 mmol) diethylamine, the reaction mixture was stirred 5 h under argon. Excess diethylamine was removed in vacuum with a rotatory evaporator at 35° C. and 35 mmHg (left for 1 h in vacuum). The dimethylformamide solution was treated with 299.1 mg (0.32 mmol) HDP 30.1170 FmocNH-Cys(STr)-Asn(NHTr)-OH, 165.4 (0.32 mmol) PyBOP (benzotriazol-1-yl-oxytripyrrolidinophosphonium hexafluorophosphate) and 55.3 µl (0.32 mmol) N-ethyl-diisopropylamine (DIPEA). The reaction mixture was stirred under argon for 17 h and then diluted with chloroform. The organic solvents were washed with 5% citric acid (1×) and with water (3×). After drying over sodium sulphate, volatiles were evaporated and the residue purified on a silica gel column with a gradient of n-hexane to ethyl acetate. The product fractions were collected and evaporated to a white solid. Yield: 249 mg (57%) of HDP 30.1668.

MS (ESI$^+$) found: 1372.15 [MH]$^+$; calc.: 1371.60 ($C_{84}H_{85}N_5O_{11}S$)

MS (ESI$^+$) found: 1394.73 [M+Na]$^+$; calc.: 1394.60 ($C_{84}H_{85}N_5NaO_{11}S$)

3.5 Synthesis of HDP 30.1606

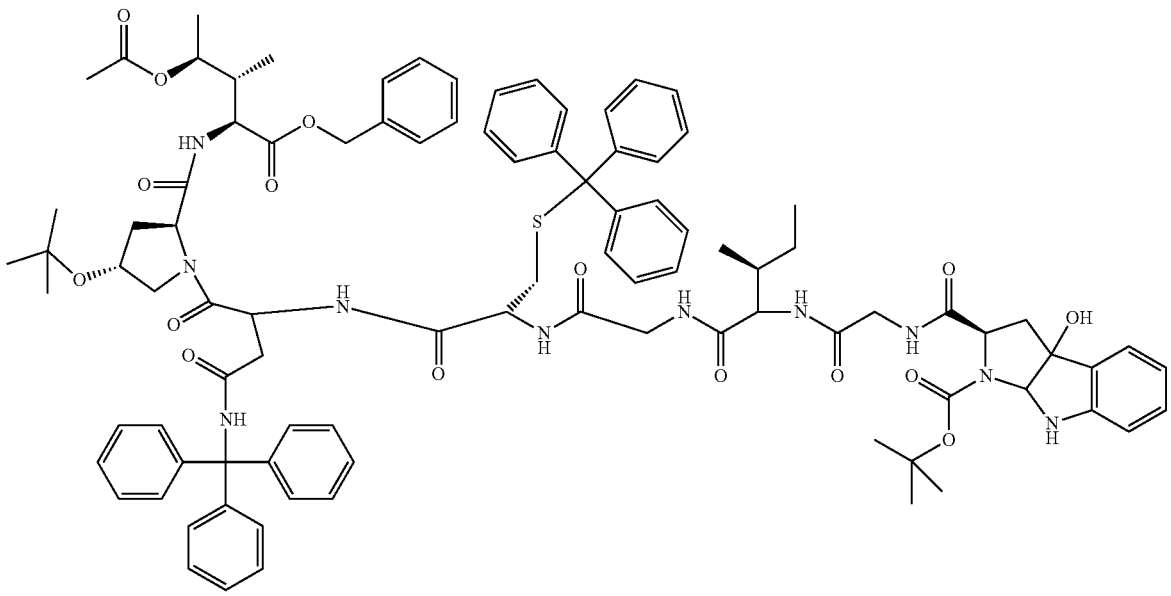

HDP 30.1606

248.0 mg (0.18 mmol) HDP 30.1668 were dissolved in 8 ml dry dimethylformamide. After addition of 52.6 μl (0.51 mmol) diethylamine the reaction mixture was stirred 4.5 h at room temperature under argon. Excess diethylamine was removed in vacuum with a rotatory evaporator at 37° C. and 37 mmHg (left for 1 h of evacuation). Then the dimethylformamide solution was treated with 98.9 mg (0.18 mmol) HDP 30.0287 BocHpi-Gly-Ile-Gly-OH, 94.1 (0.18 mmol) PyBOP (benzotriazol-1-yl-oxytripyrrolidinophosphonium hexafluorophosphate) and 31.5 μl (0.18 mmol) N-ethyldiisopropylamine (DIPEA) and stirred under argon for 17 h. The DMF solution was diluted with chloroform and washed with 5% citric acid (1×) and with water (3×). After drying over sodium sulphate the volatiles were evaporated and the residue (398.0 mg) purified on a silica gel column with a linear gradient of $CHCl_3$ to $CHCl_3/MeOH$ (15/1). The product fractions were collected and the solvents evaporated to yield a white solid (228.2 mg (75%)).

MS (ESI$^+$) found: 1679.28 [MH]$^+$; calc.: 1678.78 ($C_{95}H_{110}N_{10}O_{16}S$)

MS (ESI$^+$) found: 1701.68 [M+Na]$^+$; calc.: 1701.78 ($C_{95}H_{110}N_{10}NaO_{16}S$)

3.6 Synthesis of HDP 30.1607

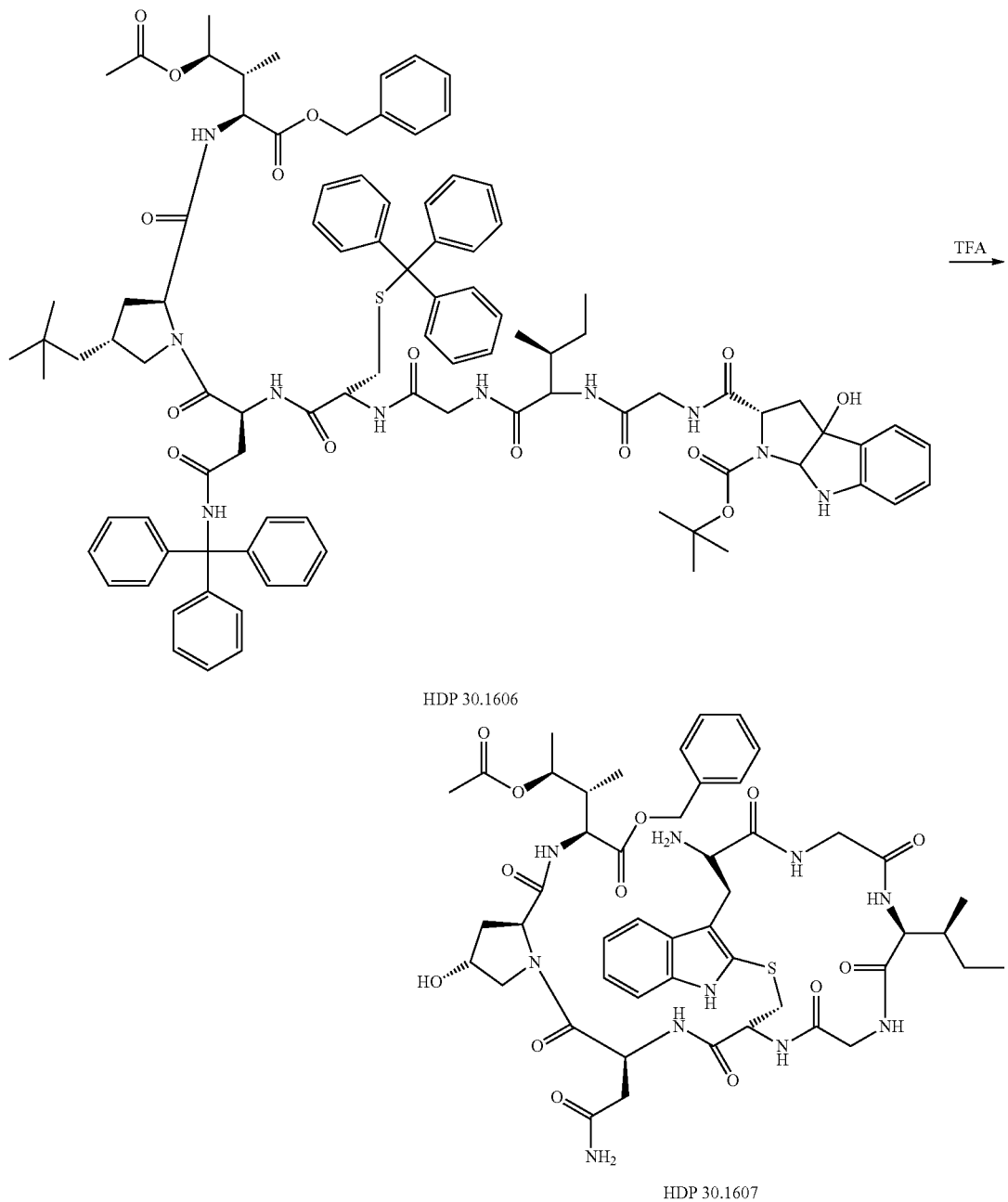

228.1 mg (0.14 mmol) HDP 30.1606 were dissolved in 10 ml trifluoroacetic acid (TFA). The clear solution was stirred under argon for 5 h and evaporated to dryness (rotatory evaporator at 35° C.). The residue was evaporated with methanol (3×) to remove traces of trifluoroacetic acid. The remaining residue (254.2 mg) was purified by RP18 HPLC (Luna™ 10μ, 250×21 mm, Phenomenex®, 230 nm) with a gradient of 95% H₂O/5% MeOH/0.05% TFA to 95% MeOH/5% H₂O/0.05% TFA and a flow rate of 15 ml/min. Pure fractions were evaporated and freeze dried in water: 65.1 mg (47%) of HDP 30.1607 as an amorphous solid.

MS (ESI⁺) found: 1021.53 [MH]⁺; calc.: 1020.44 ($C_{48}H_{64}N_{10}O_{13}S$)

MS (ESI⁺) found: 1043.63 [M+Na]⁺; calc.: 1043.44 ($C_{48}H_{64}N_{10}NaO_{13}S$)

3.7 Synthesis of HDP 30.1676

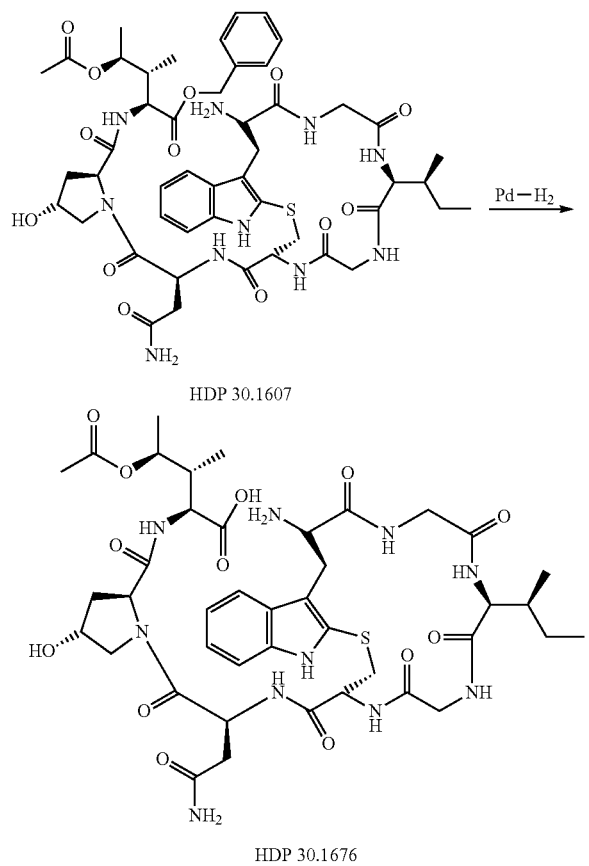

HDP 30.1607

HDP 30.1676

12.3 mg (12.06 μmol) HDP 30.1676 were dissolved in a mixture of 4 ml ethanol and 0.2 ml acetic acid. After addition of 25 mg Pd/C (10%), the reaction flask was charged with hydrogen. Hydrogenation was carried out at room temperature under normal pressure. After 4 h the TLC control (SiO₂:CHCl₃/MeOH/H₂O (65/25/4) shows completion of the debenzylation. The catalyst was filtered off and the reaction mixture was evaporated to dryness. The crude product was purified by RP18 HPLC (Luna™ 10μ, 250×21 mm, Phenomenex®, 230 nm) with a gradient of 95% H₂O/5% MeOH/0.05% TFA to 95% MeOH/5% H₂O/0.05% TFA and a flow rate of 15 ml/min. The pure fraction was evaporated to dryness and freeze dried in water yielding 5.64 mg (50%) HDP 30.1676 as an amorphous solid.

MS (ESI⁺) found: 931.48 [MH]⁺; calc.: 930.39 ($C_{41}H_{58}N_{10}O_{13}S$)

MS (ESI⁺) found: 953.59 [M+Na]⁺; calc.: 953.39 ($C_{41}H_{58}N_{10}NaO_{13}S$)

3.8 Synthesis of HDP 30.1679

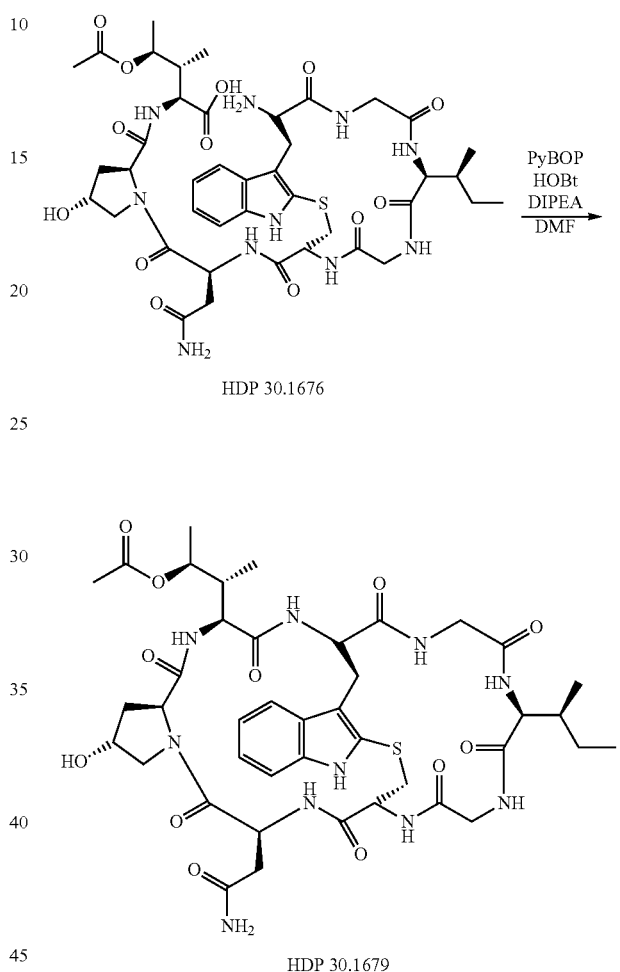

HDP 30.1676

HDP 30.1679

32.6 mg (35.0 μmol) seco-peptide HDP 30.1676 were dissolved in 36 ml dry dimethylformamide (DMF) and subsequently treated at room temperature under argon atmosphere with 54.7 mg (105.1 μmol) PyBOP (benzotriazol-1-yl-oxytripyrrolidinophosphonium hexafluorophosphate), 16.09 mg (105.1 μmol) N-hydroxybenzotriazole hydrate (HOBt×H₂O) and 36.6 μl (210.0 μmol) N-ethyl-diisopropylamine (DIPEA). The reaction mixture was stirred 23 h at ambient temperature under argon. The volatiles were removed in high vacuum (0.26 mm Hg at 39° C.) and the residue purified by RP18 HPLC (Luna™ 10μ, 250×21 mm, Phenomenex®, 230 nm) with a gradient of 95% H₂O/5% MeOH/0.05% TFA to 95% MeOH/5% H₂O/0.05% TFA and a flow rate of 15 ml/min. The pure fraction was evaporated and freeze dried in water to give 11.1 mg (35%) HDP 30.1679 as an amorphous solid.

MS (ESI⁺) found: 913.44 [MH]⁺; calc.: 912.38 ($C_{41}H_{56}N_{10}O_{12}S$)

MS (ESI⁺) found: 935.58 [M+Na]⁺; calc.: 935.38 ($C_{41}H_{56}N_{10}NaO_{12}S$)

3.9 Synthesis of HDP 30.1790

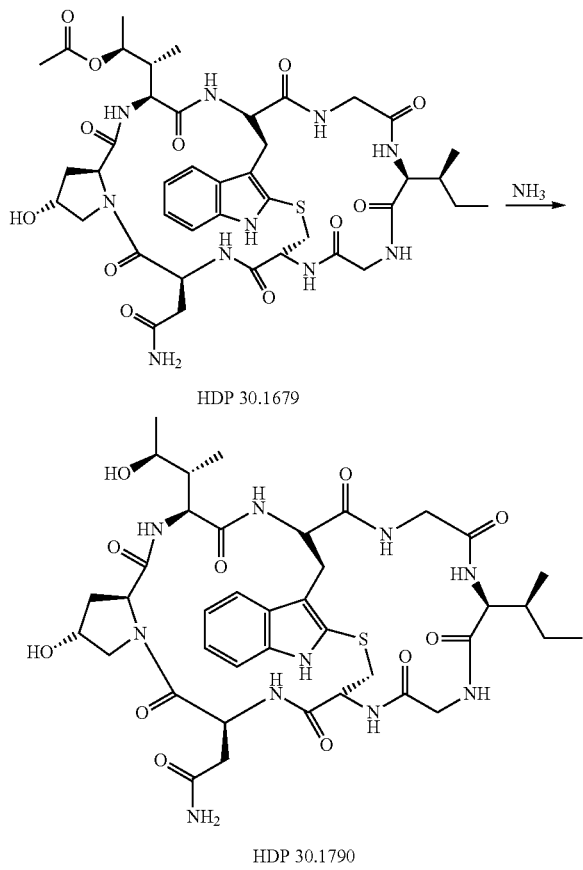

HDP 30.1679

HDP 30.1790

11.0 mg (12.1 mmol) HDP 30.1679 were dissolved in 1800 µl of a 7-molar solution of ammonia in anhydrous methanol. The reaction flask was flushed with argon, sealed and stirred for 48 h at room temperature. The reaction mixture was evaporated to dryness and the remaining residue (13.9 mg) purified by RP18 HPLC (Luna™ 10µ, 250×21 mm, Phenomenex®, 230 nm) with a gradient of 95% H$_2$O/5% MeOH/0.05% TFA to 95% MeOH/5% H$_2$O/0.05% TFA and a flow rate of 15 ml/min. The product fraction was evaporated and freeze dried in water to 4.56 mg (44%) HDP 30.1790 as a white, amorphous solid.

MS (ESI$^+$) found: 871.51 [MH]$^+$; calc.: 870.37 (C$_{39}$H$_{54}$N$_{10}$O$_{11}$S)

MS (ESI$^+$) found: 893.69 [M+Na]$^+$; calc.: 893.37 (C$_{39}$H$_{54}$N$_{10}$NaO$_{11}$S)

The invention claimed is:

1. A method for synthesizing a compound of formula 6 (2S,3R,4S)—CH$_3$—CH(OR$^1$)—CH(CH$_3$)—CH(NHR$^2$)—C(=O)OR$^3$, wherein R$^1$ is C(=O)—R$^{1'}$, wherein R$^{1'}$ is alkyl, comprising the steps of (a) complexing the compound 5 (2S,3R,4S)-L-4-hydroxyisoleucine with copper or boron compounds; (b) acylation of the 4-hydroxy group of the resulting compound from step (a) with a compound R$^{1'}$—C(=O)—X, wherein X is a leaving group; (c) cleavage of the metal complex resulting from step (b); (d) protection of the α-amino group with an R$^2$ group, wherein the R$^2$ group is an Fmoc group; and (e) protection of the carboxyl group with an R$^3$ group, wherein the R$^3$ group is a benzyl group or t-butyl group.

2. The method of claim 1, wherein the complexing of compound 5 (2S,3R,4S)-L-4-hydroxyisoleucine in step (a) is with the boron compound, wherein the boron compound is 9-borabicyclo [3,3,1] nonan (9-BBN).

3. The method of claim 1, wherein in step (b), R$^{1'}$ is C$_{1-6}$-alkyl.

4. The method of claim 1, wherein in step (b), R$^{1'}$ is methyl.

* * * * *